United States Patent [19]

Hall et al.

[11] Patent Number: 4,560,698

[45] Date of Patent: Dec. 24, 1985

[54] 7-OXABICYCLOHEPTANE SUBSTITUTED THIO PROSTAGLANDIN ANALOGS AND THEIR USE IN THE TREATMENT IN THROMBOLYTIC DISEASE

[75] Inventors: Steven E. Hall, Ewing Township, Mercer County; Martin F. Haslanger, Lambertville, both of N.J.

[73] Assignee: E. R. Squibb & Sons, Inc., Princeton, N.J.

[21] Appl. No.: 617,201

[22] Filed: Jun. 4, 1984

[51] Int. Cl.[4] .................. A61K 31/34; C07D 307/00
[52] U.S. Cl. ..................... 514/469; 549/463
[58] Field of Search ............... 549/463; 424/285; 514/469

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS 0043292 8/1982 European Pat. Off. .
2039909 8/1980 United Kingdom .

*Primary Examiner*—Henry R. Jiles
*Assistant Examiner*—Bernard I. Dentz

*Attorney, Agent, or Firm*—Lawrence S. Levinson; Burton Rodney

[57] ABSTRACT

7-Oxabicycloheptane substituted thio prostaglandin analogs are provided having the structural formula

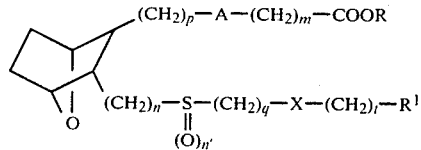

wherein p is 0 to 4; A is CH=CH, $(CH_2)_2$, or a single bond; m is 0 to 8; R is H, lower alkyl, alkali metal or tris(hydroxymethyl)aminomethane; n is 1 to 4; n' is 0, 1 or 2; q is 1 to 12; X is

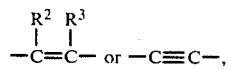

wherein $R^2$ and $R^3$ may be the same or different and are H or lower alkyl; t is 0 to 5; and $R^1$ is H, lower alkyl, aryl, aralkyl, cycloalkyl or cycloalkylalkyl, and including all stereoisomers thereof.

The compounds are cardiovascular agents and antiinflammatory agents useful, for example, in the treatment of thrombolytic disease, inflammation and pain.

16 Claims, No Drawings

7-OXABICYCLOHEPTANE SUBSTITUTED THIO PROSTAGLANDIN ANALOGS AND THEIR USE IN THE TREATMENT IN THROMBOLYTIC DISEASE

DESCRIPTION OF THE INVENTION

The present invention relates to 7-oxabicycloheptane thio prostaglandin analogs which are cardiovascular agents useful, for example, in the treatment of thrombolytic disease, and antiinflammatory agents as well as analgesic agents. These compounds have the structural formula

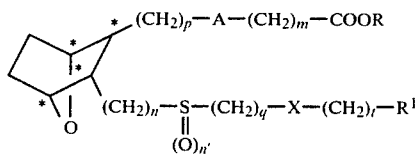

and including all stereoisomers thereof, wherein p is 0 to 4; A is CH=CH, $(CH_2)_2$, or a single bond; m is 0 to 8; R is H, lower alkyl, alkali metal or tris(hydroxymethyl)aminomethane; n is 1 to 4; n' is 0, 1 or 2; q is 1 to 12; X is

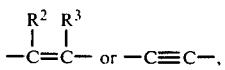

wherein $R^2$ and $R^3$ may be the same or different and are H or lower alkyl; t is 0 to 5; and $R^1$ is H, lower alkyl, aryl, aralkyl, cycloalkyl or cycloalkylalkyl.

Thus, the compounds of formula I include the following types of compounds:

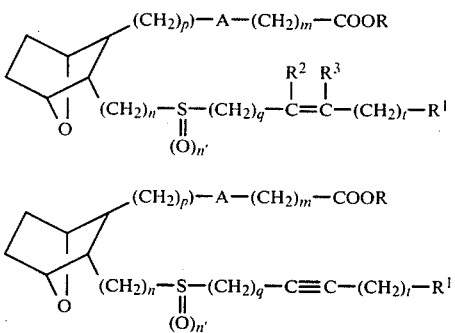

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, a haloaryl substituent, a cycloalkyl substituent (that is, cycloalkylalkyl) or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The term "aralkyl", "aryl-alkyl" or "aryl-lower alkyl" as used herein refers to lower alkyl groups as discussed above having an aryl substituent, such as benzyl.

The terms "$(CH_2)_p$", "$(CH_2)_m$", "$(CH_2)_n$", "$(CH_2)_q$" and "$(CH_2)_t$" include a straight or branched chain radical having from 1 to 8 carbons in the normal chain in the case of "$(CH_2)_m$", 1 to 4 carbons in the normal chain in the case of "$(CH_2)_n$" and "$(CH_2)_p$", 1 to 12 carbons in the normal chain in the case of $(CH_2)_q$, and 1 to 5 carbons in the normal chain in the case of "$(CH_2)_t$" and may contain one or more lower alkyl substituents. Examples of $(CH_2)_m$, $(CH_2)_n$, $(CH_2)_p$, $(CH_2)_q$ and $(CH_2)_t$ groups include

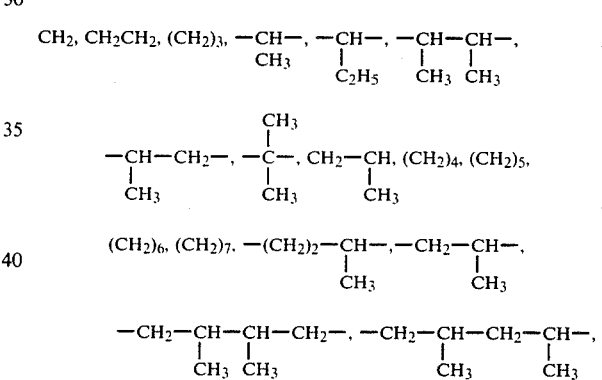

and the like.

Preferred are those compounds of formula I wherein p is 1, A is $(CH_2)_2$ or CH=CH, m is 2 to 4, R is H, n is 0, 1 or 2, q is 1 to 2, X is

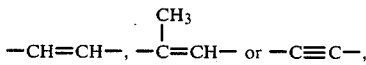

t is 0, 1 or 2, and $R^1$ is H, methyl, hexyl, cyclohexyl, phenyl or benzyl.

The various compounds of the invention may be prepared as outlined below.

A. Where p = 1, n = 1, A is CH=CH

-continued
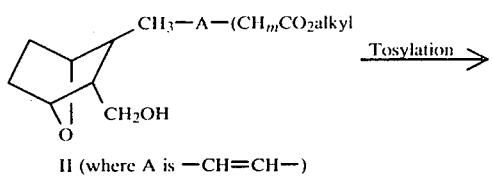
II (where A is —CH=CH—)
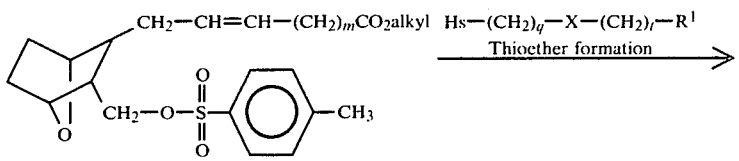
III
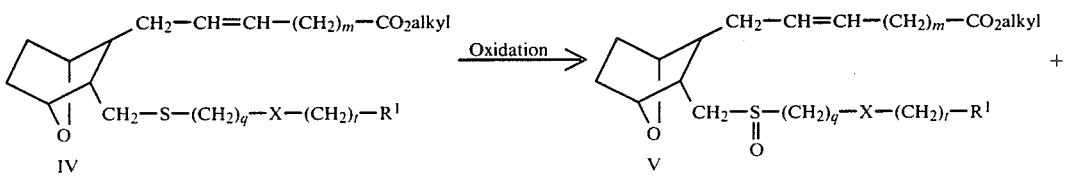
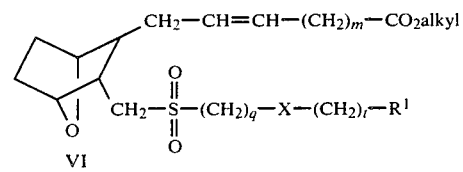
VI
B. Where p is 1, n is 1, A is (CH$_2$)$_2$ or a single bond (in which case m is 3 to 8)
II $\xrightarrow[\text{H}_2/\text{Pd/C}]{\text{Reduction}}$ 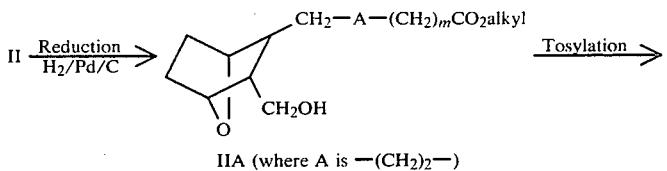
IIA (where A is —(CH$_2$)$_2$—)
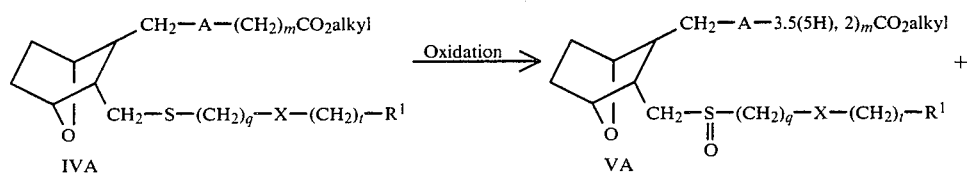
IIIA (where A is —(CH$_2$)$_2$—)

-continued
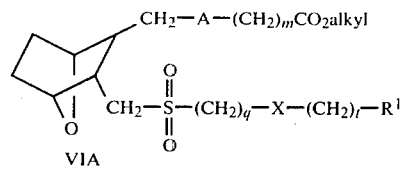
A. (A is CH=CH)
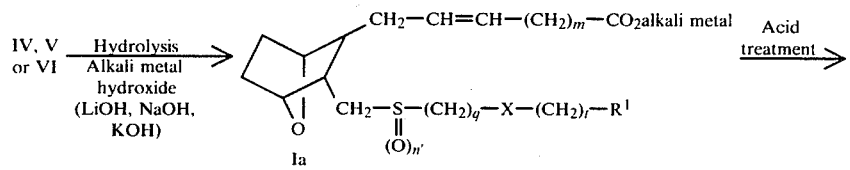
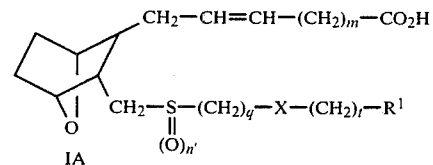
B. (A is $(CH_2)_2$ or a single bond)
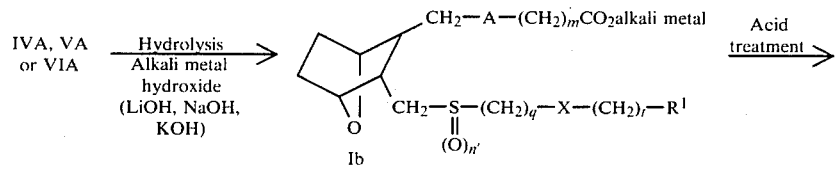
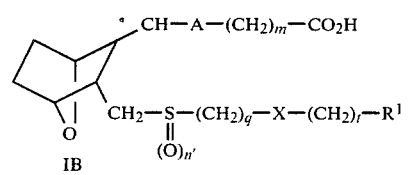
C. Where p is 1 and n is 2 to 4
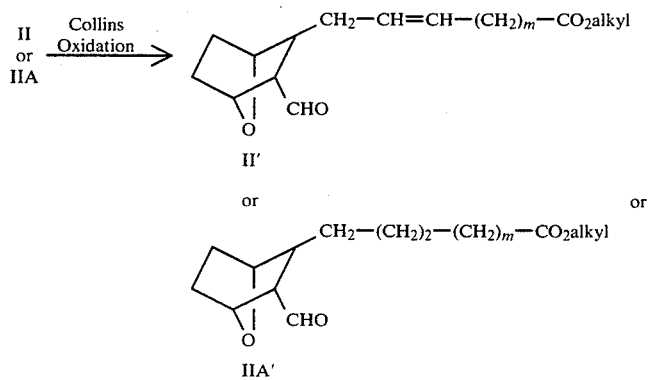

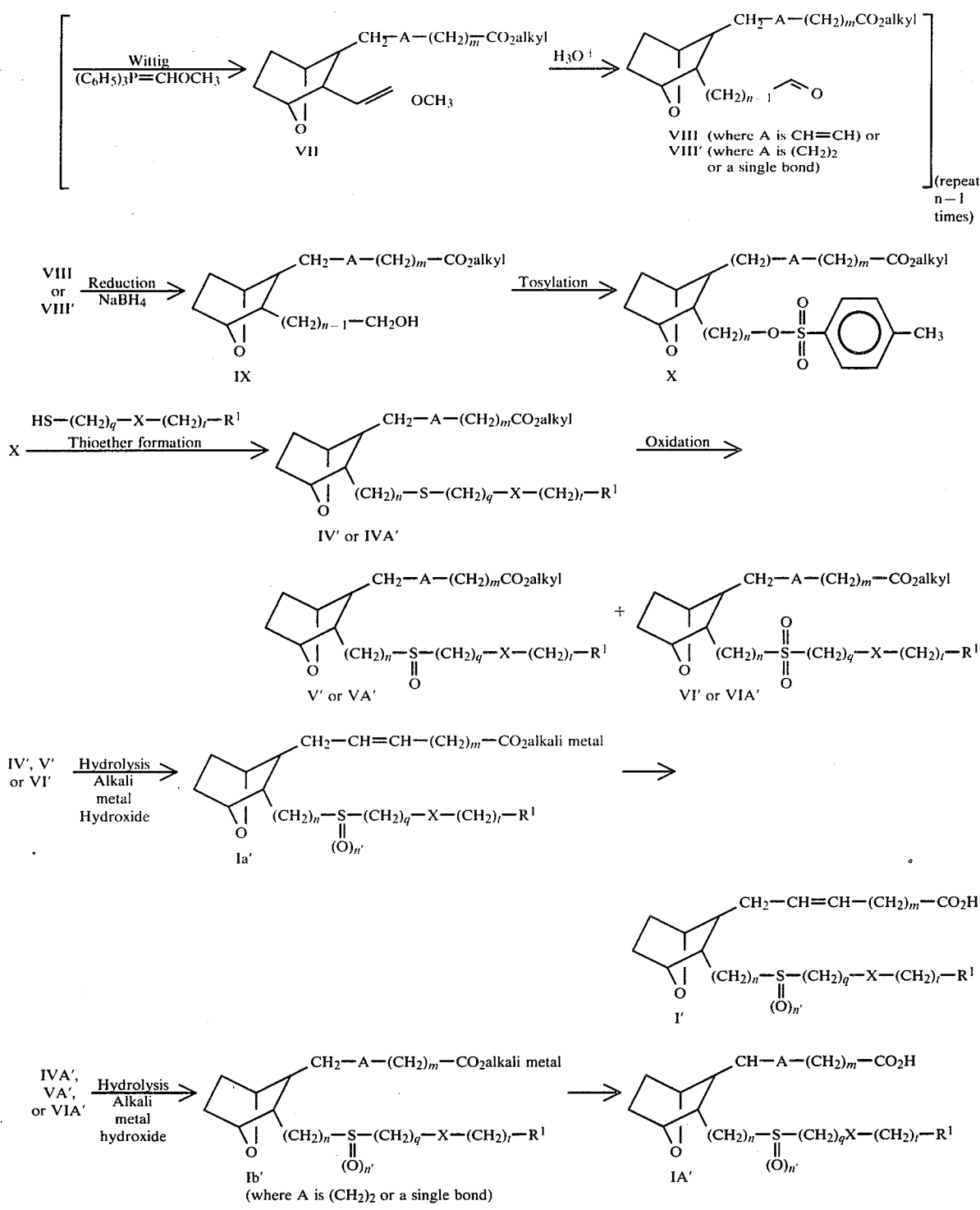
D. Where p = 0, A is —CH=CH—, n is 1
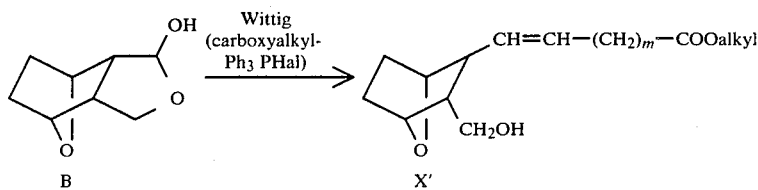

-continued
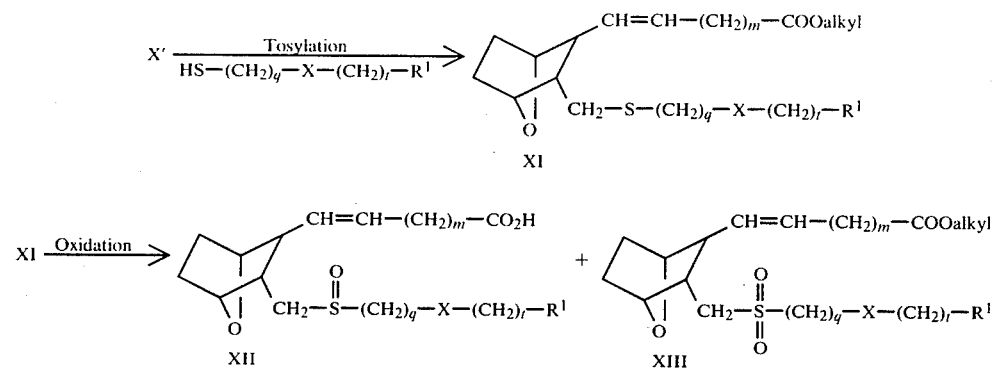
E. Where p = 0, A is —(CH$_2$)$_2$—, n is 1
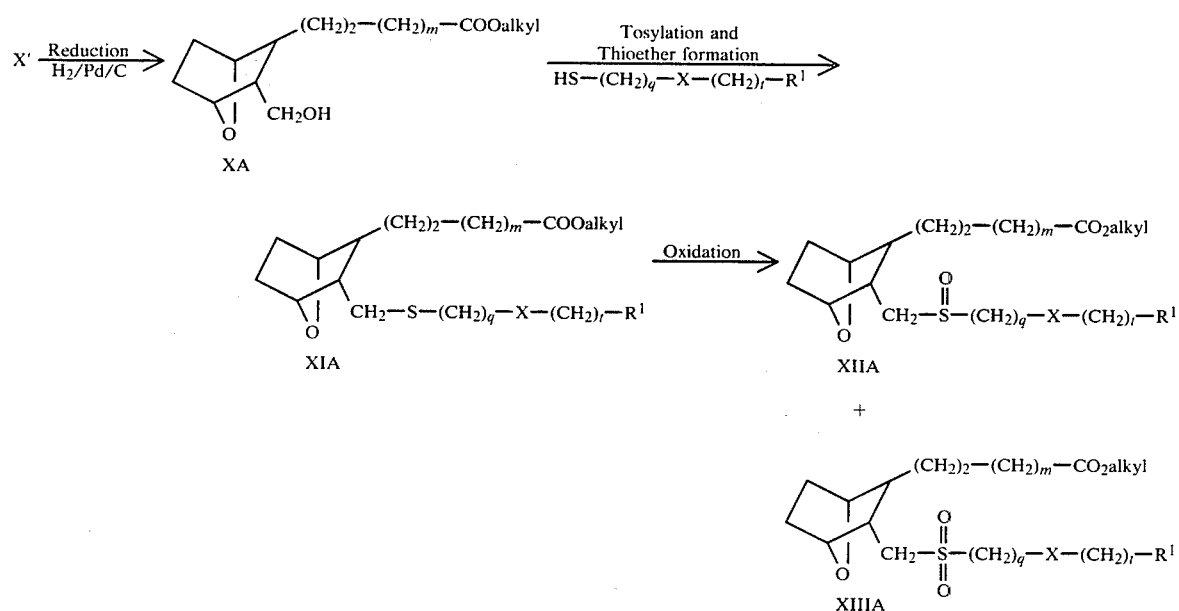
F. Where p is 2, n is 1, A is —CH=CH—
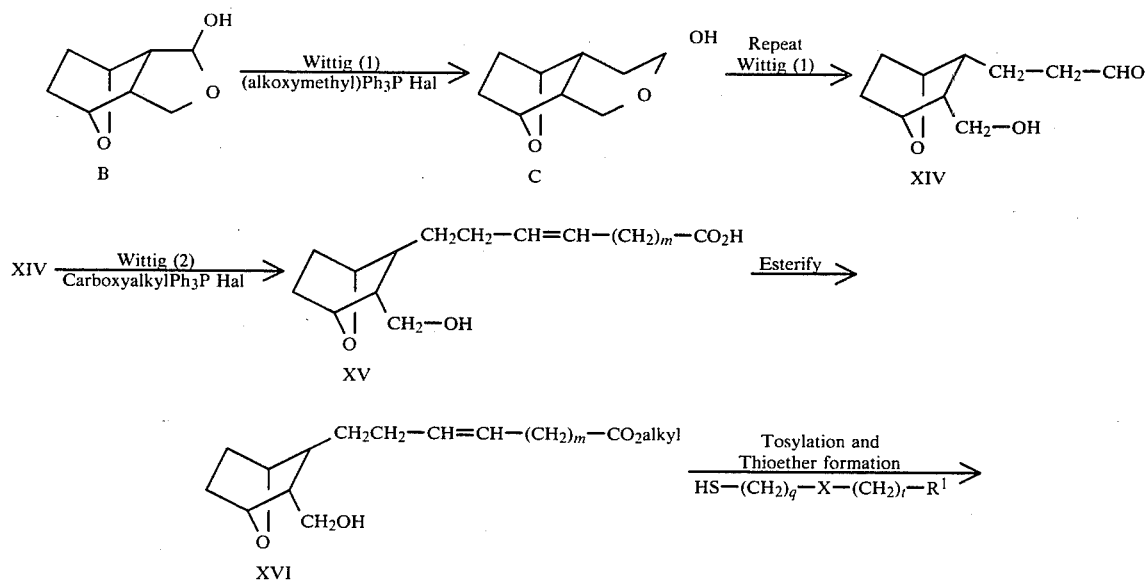

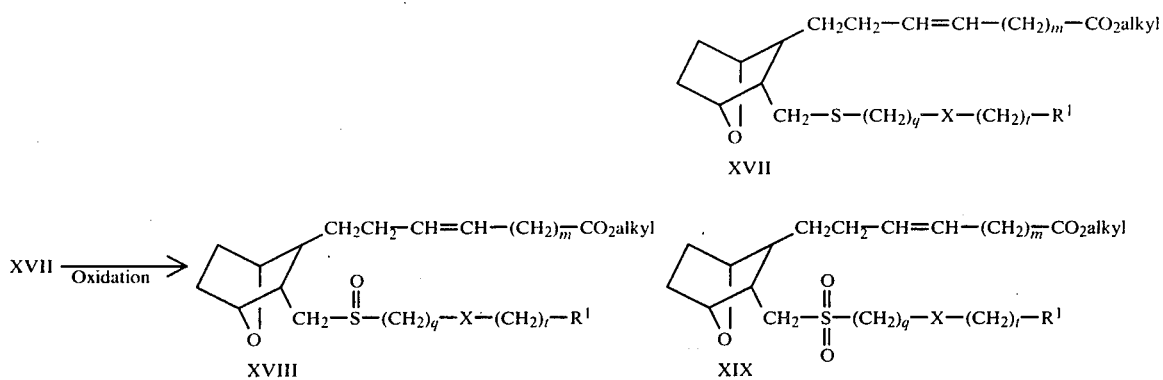
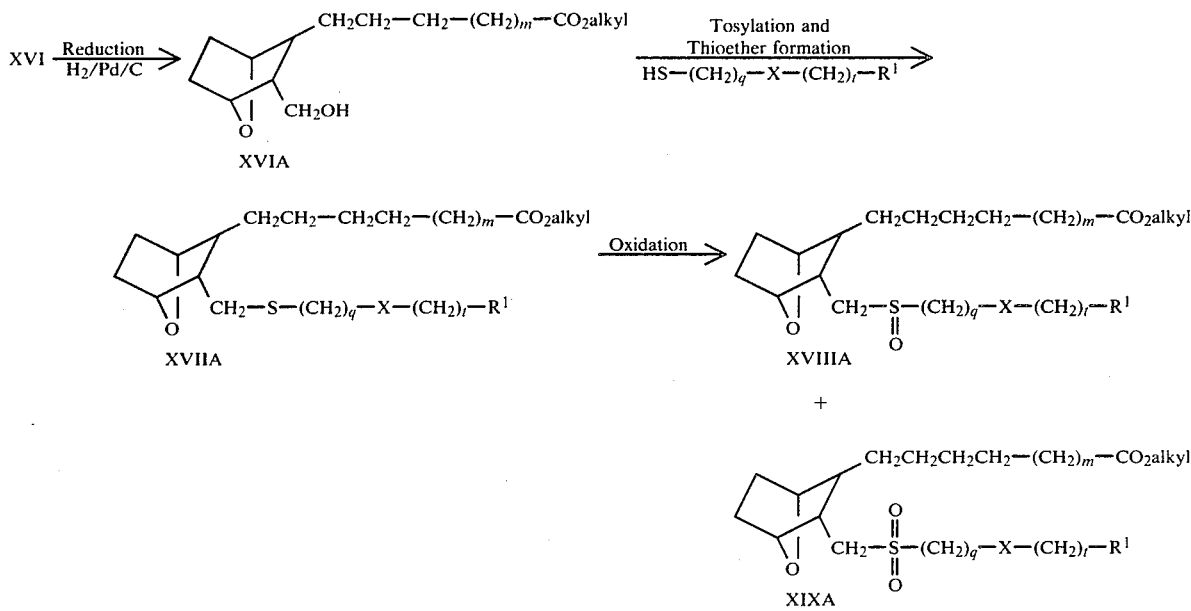
G. p is 2, n is 1, A is —CH$_2$—CH$_2$—
H. Where p is 3 or 4, n is 1, A is —CH=CH—
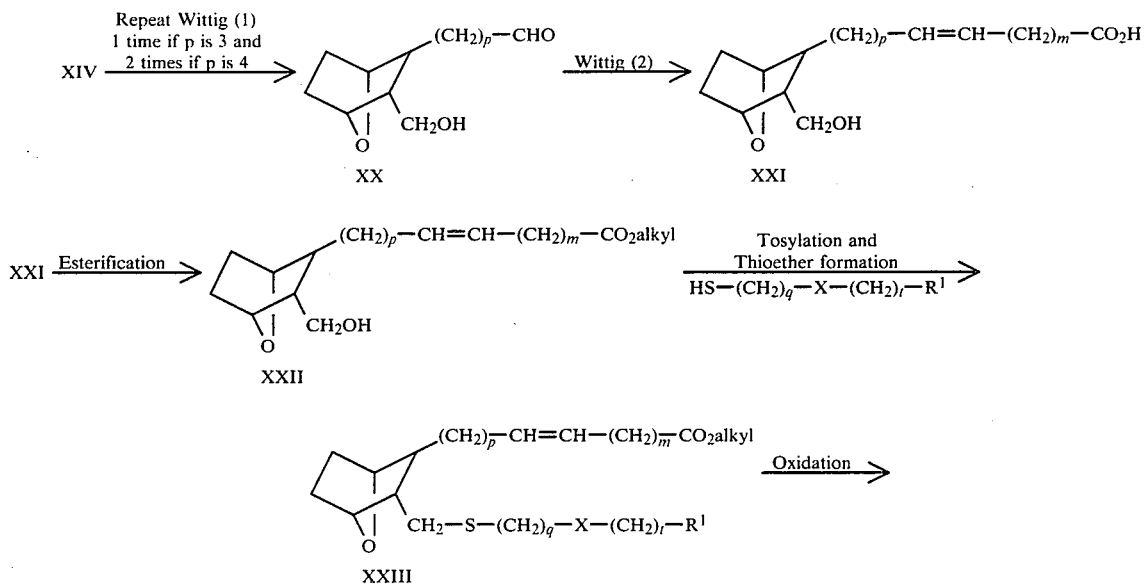

-continued

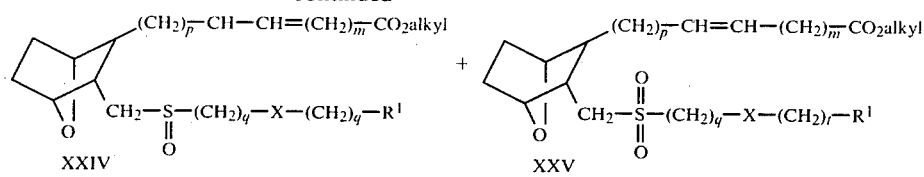

I. Where p is 3 or 4, n is 1, A is CH₂CH₂

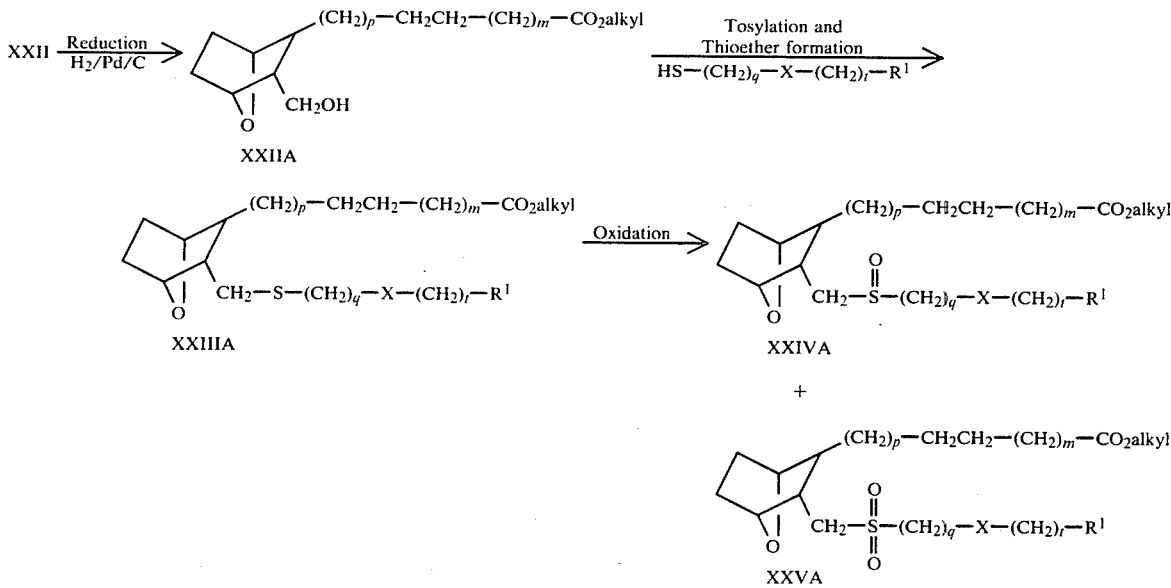

J.

$$\left.\begin{array}{l}\text{XI}\\ \text{XII}\\ \text{XIII}\\ \text{XIA}\\ \text{XIIA}\\ \text{XIIIA}\\ \text{XVII}\\ \text{XVIII}\\ \text{XIX}\\ \text{XVIIA}\\ \text{XVIIA}\\ \text{XIXA}\\ \text{XXIII}\\ \text{XXIV}\\ \text{XXV}\\ \text{XXIIIA}\\ \text{XXIVA}\\ \text{XXVA}\end{array}\right\} \xrightarrow{\text{Hydrolysis}} \text{corresponding acid}$$

In the reaction sequence identified as "A", and "B" where in Formula I p is 1 and n is 1, the lower alkyl ester containing the hydroxymethyl group, that is, compound II (where A is —CH=CH—, reaction sequence "A") or IIA (where A is —(CH₂)₂, reaction sequence "B") (prepared as described in U.S. Pat. No. 4,143,054) is employed as the starting material. Thus, where A is —CH=CH— (reaction sequence "A"), compound II is subjected to a tosylation reaction, for example, by reacting II with tosyl chloride in pyridine to form tosylate III. To form the tosylate IIIA (where A is (CH₂)₂) (reaction sequence "B"), compound II is reduced, for example with hydrogen over a palladium on carbon catalyst, to form hydroxymethyl compound IIA (where A is (CH₂)₂ or a single bond in which case m is 3 to 8) and compound IIA is subjected to a tosylation reaction to form tosylate IIIA (where A is (CH₂)₂). Thereafter, tosylate III or IIIA is reacted with a thiol of the structure $$\text{HS—(CH}_2)_q\text{—X—(CH}_2)_r\text{—R}^1 \qquad \text{A}$$

employing a molar ratio of III or IIIA:thiol of within the range of from about 0.8:1 to about 1:4, in a solvent such as tetrahydrofuran and in the presence of potassium t-butoxide to form the sulfide IV or IVA.

To form the sulfinyl and/or sulfonyl analogs (where n=1), sulfide derivative IV or IVA is subjected to oxidation, for example by reacting same with sodium periodate, in the presence of methanol and tetrahydrofuran, to form the sulfinyl derivative V or VA and the sulfonyl derivative VI or VIA. The above sulfinyl and sulfonyl derivatives may be separated by chromatography or other conventional separation procedures.

In the reaction sequence identified as "C", where in Formula I n is 2 to 4, the starting lower alkyl ester containing the hydroxymethyl group, that is, compound II, (prepared as described in U.S. Pat. No. 4,143,054) is used to form the aldehyde II' (where A is —CH=CH—) or IIA' (where A is —(CH$_2$)$_2$ or a single bond). Thus, to form aldehyde II' where A is —CH=CH—, compound II is subjected to a Collins oxidation, for example, by reacting II with chromium trioxide in pyridine. To form the aldehyde IIA' (where A is (CH$_2$)$_2$ or a single bond), compound II is reduced, for example with hydrogen over a palladium on carbon catalyst, to form hydroxymethyl compound IIA (where A is (CH$_2$)$_2$ or a single bond) and compound IIA is subjected to a Collins oxidation to form aldehyde IIA' (where A is (CH$_2$)$_2$ or a single bond).

The aldehyde II' or IIA' is used to prepared aldehyde VIII or VIII' (where n is 2–4) by carrying out a homologation sequence, such as a Wittig reaction with (C$_6$H$_5$)$_3$P=CHOMe followed by hydrolysis, (n−1) times. The aldehyde VIII (where n is 2–4 and A is CH=CH) or VIII' (where n is 2 to 4 and A is (CH$_2$)$_2$ or a single bond in which case m is 3 to 8) is thus carried on to compounds of this invention where n is 2–4, that is

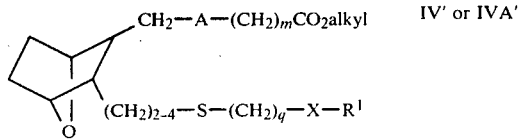

(IV' where A is —CH=CH—)
(IVA' where A is (CH$_2$)$_2$ or a single bond)
by reducing aldehyde VIII or VIII' employing a reducing agent such as sodium borohydride or sodium cyanoborohydride in a solvent such as methanol to form the alcohol ester IX which is subjected to a tosylation reaction as described above to form tosylate X which in turn is subjected to thioether formation by reaction with

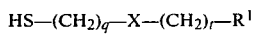     A as described above to form sulfide IV' or IVA'.

The sulfinyl derivative (where n is 2 to 4) and sulfonyl derivatives (where n is 2 to 4) are prepared by subjecting sulfide IV' or IVA' to an oxidation reaction as described above to form a mixture of sulfinyl V' and/or VA', and sulfonyl VI' and/or VIA'.

The above sulfinyl and sulfonyl derivatives may be separated by chromatography or other conventional separation procedures.

Referring now to reaction sequence "D", compounds of the invention wherein p is 0 and A is —CH=CH—, that is, compound XI may be prepared by subjecting compound B (prepared as described in Example 3 of U.S. Pat. No. 4,143,054) to a Wittig reaction, for example, as described in Example 6(c) of U.S. Pat. No. 4,143,054, by reacting B with a carboxyalkyltriphenyl phosphonium halide, such as carboxypentyltriphenyl phosphonium bromide to form the hydroxymethyl compound X' which may then be subjected to tosylation and thioether formation as described hereinbefore to form the ester XI which, in turn, may be oxidized to the esters XII and XIII.

As seen in reaction sequence "E", where it is desired to prepare compounds of the invention wherein p is 0 and A is (CH$_2$)$_2$, the hydroxymethyl compound X is reduced by treatment with hydrogen in the presence of a palladium on carbon catalyst to form hydroxymethyl compound XA which may then be tosylated and subjected to thioether formation to form ester XIA which then may be oxidized to esters XIIA and XIIIA.

Compounds of the invention wherein p is 2, A is —CH=CH— and n is 1 may be prepared as outlined in reaction sequence "F" by subjecting starting compound B to a Wittig reaction, referred to as Wittig (1), by reacting B with an alkoxymethyltriphenyl phosphonium halide, such as (methoxymethyl)triphenylphosphonium chloride, for example, as described in Example 4 of U.S. Pat. No. 4,143,054, to form compound C. The Wittig (1) procedure is repeated on compound C to form aldehyde compound XIV. Aldehyde XIV is then subjected to a Wittig (2) procedure wherein XIV is reacted with a carboxyalkyltriphenylphosphonium halide, such as carboxypentyltriphenylphosphonium bromide, to form hydroxymethyl compound XV. Compound XV is esterified, for example, by reacting with diazomethane, to form ester XVI which is subjected to tosylation and thioether formation as described above to form ester XVII which, in turn, may be oxidized to the acids XVIII and XIX.

Compounds of the invention wherein p is 2, A is —CH$_2$—CH$_2$— and n is 1 may be prepared as outlined in reaction sequence "G" by reducing hydroxymethyl compound XVI to form compound XVIA which is then tosylated and subjected to thioether formation to form ester XVIIA which may then oxidized to form esters XVIIIA and XIXA as described hereinbefore.

Referring to reaction sequence "H", compounds of the invention wherein p is 3 or 4, A is —CH=CH— and n is 1 may be prepared by subjecting aldehyde XIV to the Wittig (1) procedure one time in the case where p is 3 and a second time in the case where p is 4, to form the aldehyde XX. Aldehyde XX is then subjected to the Wittig (2) procedure to form acid XXI which is esterified to form ester XXII which is tosylated and subjected to thioether formation as described above to form ester XXIII. Ester XXIII may then be oxidized to form esters XXIV and XXV.

As seen in reaction sequence "I", compounds of the invention wherein p is 3 or 4, A is CH$_2$CH$_2$ and n is 1 may be prepared by reducing hydroxymethyl compound XXII to form compound XXIIA which is then tosylated and subjected to thioether formation to form ester XXIIIA which, in turn, may be oxidized to form esters XXIVA and XXVA.

Compounds of the invention wherein p is 0, 2, 3 or 4 and n is 2, 3 or 4 may be prepared by substituting hydroxymethyl compound X', XA, XVI, XVIA, XXII or XXIIA in place of hydroxymethyl compound II or IIA in reaction sequences A and B.

The esters IV, V, VI, IVA, VA, VIA, IV', V', VI', IVA', VA', VIA', XI, XII, XIII, XIA, XIIA, XIIIA, XVII, XVIII, XIX, XVIIA, XVIIIA, XIXA, XXIII, XXIV, XXV, XXIIIA, XXIVA and XXVA can be converted to the free acid, that is, to I (A is CH=CH) or I' (A is (CH$_2$)$_2$ or a single bond)

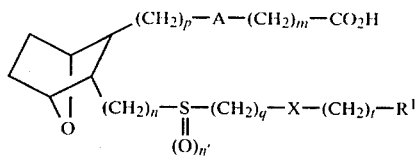

by treating the esters with an alkali metal hydroxide, such as lithium or sodium hydroxide to form the alkali metal salt Ia or Ib or Ia' or Ib', followed by neutralization with an acid, such as dilute hydrochloride acid or oxalic acid to form the acid.

The tris(hydroxymethyl)aminomethane salt of any of the acids of formula I of the present invention is formed by reacting a solution of such acid in an inert solvent such as methanol with tri(hydroxymethyl)aminomethane and thereafter the solvent is removed by evaporation to leave the desired salt.

The starting thiol A is generally known and may be conveniently prepared from the corresponding alcohols B

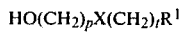     B by the general formula of Volante et al., *Tetrahedron Letters*, 1981, 22, 3119.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

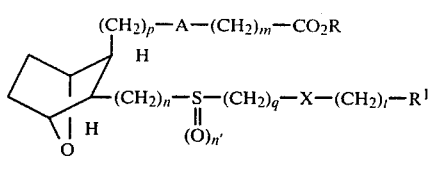

(cis-endo)

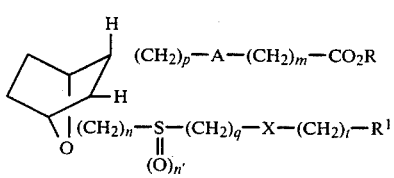

(cis-exo)

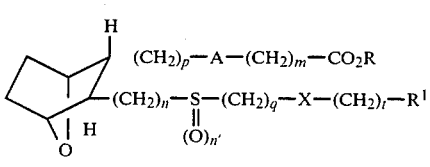

(trans)

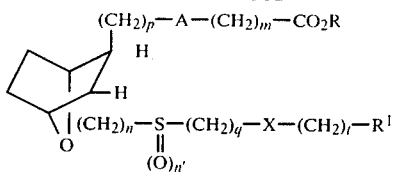

(trans)

The nucleus in each of the compounds of the invention is depicted as

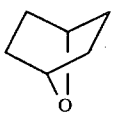

for matter of convenience; it will also be appreciated that the nucleus in the compounds of the invention may be depicted as

The compounds of this invention are cardiovascular agents useful as platelet aggregation inhibitors of arachidonic acid induced platelet aggregation, e.g., for treatment of thrombolytic disease, such as coronary or cerebral thromboses, and as inhibitors or broncho-constriction associated with asthma. They are also selective thromboxane $A_2$ receptor antagonists and synthetase inhibitors, e.g., having a vasodilatory effect for treatment of myocardial ischemic disease, such as angina pectoris. The compounds of the invention are also arachidonic acid cyclooxygenase inhibitors and are useful as analgesic agents in the manner of aspirin and indomethacin. In addition, the compounds of the invention are useful as antiinflammatory agents in the manner of indomethacin and phenylbutazone as indicated by carragenin-induced edema in the rat [Ref: Winter et al. J. Pharmacol, Exp. Ther. 141:369, 1963] and they may be used to decrease joint swelling, tenderness, pain and stiffness in conditions such as rheumatoid arthritis.

They can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the present invention. Unless otherwise indicated, all temperatures are expressed in degrees Centigrade.

EXAMPLE 1

[1β,2α(Z),3α(E),4β]-7-[3-[[(3-Phenyl-2-propenyl)thio]-methyl]-7-oxabicyclo[2.2.1]hept-2-yl]-5-heptenoic acid, methyl ester

A.

[1β,2α(Z),3α,4β]-7-[3-(Hydroxymethyl)-7-oxabicyclo[2.2.1]hept-2-yl]-5-heptenoic acid (a) A mixture of N-acetylpyridinium chloride was prepared by adding 9.6 ml (136 mmole) of acetyl chloride dropwise to 56 ml of pyridine. To this was added 5.0 g (27 mmole) of (exo)-3-(2-methoxyethenyl)-7-oxabicyclo[2.2.1]heptane-2-methanol dissolved in 5 ml of pyridine. The resulting mixture was stirred at room temperature for 1.5 hours and poured into brine. The product was extracted into ether (3×200 ml); the ether extracts were washed with 5% hydrochloric acid (2×400 ml) and brine (1×200 ml) and dried over sodium sulfate. Concentration yielded a yellow oil which was purified by passage through a short column of silica gel (150 ml) with dichloromethane, yield 4.42 g of an oil.

(b) To a solution of 4.42 g (19.6 mmole) of the oil in 500 ml of tetrahydrofuran containing 50 ml of water was added 31.1 g (97.8 mmole) of mercuric acetate. The yellow suspension which formed was stirred for 10 minutes and then the entire mixture was poured into a solution containing 200 g of potassium iodide in 2 l. of water. Upon shaking, the yellow color disappeared and the mixture was extracted with benzene (3×500 ml). The combined benzene extracts were washed with potassium iodide solution and brine and dried over sodium sulfate. Concentration yielded 3.7 g of material which crystallized on standing in an ice box.

(c) A Wittig reagent was prepared in dimethyl sulfoxide (dried over calcium hydride) by adding a solution of sodium methylsulfinylmethide (prepared by heating 300 mg of sodium hydride in 60 ml of dimethyl sulfoxide at 75° until hydrogen evolution stops) dropwise to a solution of 5.32 g (12 mmole) of 4-carboxybutyl triphenylphosphonium bromide in 100 ml of dimethyl sulfoxide. After the first orange color lasting more than 10 seconds formed, an equivalent amount of base was added to form the ylide. To this deep orange solution was added a solution of the product of part (b) in 20 ml of dimethyl sulfoxide and the resulting mixture stirred at room temperature for 45 minutes. The reaction was quenched by addition of 24 mmole of acetic acid and the mixture poured into brine (300 ml) and extracted with ether (3×200 ml). Concentration of these extracts gave an oil which was stirred with saturated sodium bicarbonate solution until crystalline triphenylphosphine oxide formed in the mixture. This mixture was washed with benzene and acidified with 10% hydrochloric acid. The aqueous layer was saturated with salt and extracted with ether which on drying (sodium sulfate) and concentration gave 2.43 g of crude product. The mixture was stirred 24 hours with 10% aqueous sodium hydroxide and reisolated by acidification and ether extraction. The product was purified on 500 g of silica gel with 50/50 ethyl acetate-hexane as the eluant which gave 600 mg of acid which crystallized on standing. This was recrystallized twice from ethyl acetate-cyclohexane to yield 320 mg of [1β,2α(Z),3α,4β]-7-[3-(hydroxymethyl)-7-oxabicyclo[2.2.1]hept-2-yl]-5-heptenoic acid.

B.

[1β,2α(Z),3α,4β]-7-[3-(p-Toluenesulfonyloxymethyl)-7-oxabicyclo[2.2.1]hept-2-yl]-5-heptenoic acid, methyl ester To a solution of 300 mg (1.12 mmol) of alcohol ester from Part A in 4 ml of dry pyridine was added 427 mg (2.24 mmol) of tosyl chloride. The mixture was stirred at room temperature under an argon atmosphere for 10 hours. The reaction mixture was diluted with 300 ml of ether, washed with 1N aqueous HCl solution (3×100 ml), and 0.5N aqueous NaOH solution (3×100 ml). The ether layer was dried over anhydrous magnesium sulfate and concentrated in vacuo. Purification was effected by flash chromatography on 30 g of silica gel 60 using 50% hexane in ether as eluant to give 450 mg of title compound (95%). TLC: silica gel, 4% $CH_3OH$ in $CH_2Cl_2$, $R_f$=0.80, iodine.

C.

[1β,2α(Z),3α(E),4β]-7-[3-[[(3-Phenyl-2-propenyl)thio]-methyl]-7-oxabicyclo[2.2.1]hept-2-yl]-5-heptenoic acid, methyl ester To a stirred solution of 97.7 mg (0.86 mmol) of potassium t-butoxide in 5 ml of THF was added 0.3 ml (1.8 mmol) of cinnamyl mercaptan (crude thiol was used without purification and was prepared from cinnamyl alcohol by the method of Volante, *Tetrahedron Letters* 1981, 22, 3119). After the reaction mixture was stirred for 10 minutes, a solution of 295 mg (0.70 mmol) of Part B tosylate in 7 ml of THF was added. The resulting yellow solution was heated to reflux (on heating a white precipitate formed) for 4 hours. The cooled reaction mixture was partitioned between 100 ml each of saturated aqueous $NaHCO_3$ and ether. The aqueous layer was extracted with 100 ml of ether. The combined ether extracts were washed with 0.5N NaOH, dried over $MgSO_4$, filtered and concentrated in vacuo to give 510 mg of crude product. Purification was effected by flash chromatography on 30 g of silica gel 60 using 4:1 hexane:ether as eluant. Fractions 26-31 were concentrated to give 220 mg (71%) of title ester. TLC: silica gel, 2:1 hexane:ether, $R_f$ 0.35, iodine.

EXAMPLE 2

[1β,2α(Z),3α(E),4β]-7-[3-[[(3-Phenyl-2-propenyl)thio]-methyl]-7-oxabicyclo[2.2.1]hept-2-yl]-5-heptenoic acid To a stirred solution of 0.22 g (0.55 mmol) of Example 1 ester in 20 ml of distilled THF and 2.6 ml of distilled $H_2O$ was added 4 ml of 1N LiOH solution. The resulting mixture was purged with a stream of dry Ar for 1 hour. After stirring for an additional 5.5 hours at room temperature, the reaction mixture was partitioned between 100 ml each of saturated NaCl solution and EtOAc. The aqueous layer was acidified to pH=3.5 by the addition of 1N aqueous HCl and then extracted with the original EtOAc layer. The aqueous layer was extracted again with 100 ml of EtOAc. The combined organic extracts were dried over $MgSO_4$, filtered, and concentratd in vacuo to afford 270 mg of crude product. Purification was effected by flash chromatography on 30 g of silica gel 60 using 1% $MeOH/CH_2Cl_2$ as eluant. Fractions 43-72 were concentrated to afford 190 mg (89%) of a mixture of double bond isomers. This product was rechromatographed on 20 g silica gel 60 using 3% MeOH/CH$_2$Cl$_2$. Fractions 12–20 were concentrated to give 120 mg (57%) of title acid. Fractions 9–10 were concentrated to afford 50 mg of a mixture of ω-chain double bond isomers. TLC for title acid: silica gel, 3% MeOH/CH$_2$Cl$_2$, R$_f$=0.25, iodine.

Anal Calcd for C$_{23}$H$_{30}$O$_3$S: C, 71.46; H, 7.82; S, 8.30. Found: C, 71.31; H, 7.87; S, 8.26.

EXAMPLE 3

[1β,2α,3α(E),4β]-7-[3-[[(3-Phenyl-2-propenyl)thio]methyl]-7-oxabicyclo[2.2.1]hept-2-yl]heptanoic acid, methyl ester

A.

(1β,2α,3α,4β)-7-[3-(Hydroxymethyl)-7-oxabicyclo[2.2.1]hept-2-yl]heptanoic acid, methyl ester To 800 mg (3.0 mmole) of the [1β,2α(Z),3α,4β]-7-[3-(hydroxymethyl)-7-oxabicyclo[2.2.1]hept-2-yl]-5-heptenoic acid, methyl ester as prepared in Example 1, dissolved in 120 ml of ethyl acetate was added, under an argon atmosphere, 160 mg of 5% Pd on carbon. The argon atmosphere was exchanged for a slight positive pressure of hydrogen and the reaction was stirred for 8 hours at 25°, filtered through a celite plug and evaporated to provide 730 mg (90%) of the title A compound.

B.

[1β,2α,3α(E),4β]-7-[[3-[(3-Phenyl-2-propenyl)thio]methyl]-7-oxabicyclo[2.2.1]hept-2-yl]heptanoic acid, methyl ester Following the procedure of Example 1 except substituting the Part A alcohol-ester for the Example 1A alcohol ester, the title product is obtained.

EXAMPLE 4

[1β,2α,3α(E),4β]-7-[3-[[(3-Phenyl-2-propenyl)thio]methyl]-7-oxabicyclo[2.2.1]hept-2-yl]heptanoic acid Following the procedure of Example 2 except substituting the Example 3 methyl ester for the Example 1 methyl ester, the title acid is obtained.

EXAMPLE 5

[1β,2α(Z),3β(E),4β]-7-[3-[[(3-Phenyl-2-propenyl)thio]methyl]-7-oxabicyclo[2.2.1]hept-2-yl]-5-heptenoic acid, methyl ester

A.

[1β,2α(Z),3β(E),4β]-7-[3-(p-Toluenesulfonyloxymethyl)-7-oxabicyclo[2.2.1]hept-2-yl]-5-heptenoic acid, methyl ester.

To a solution of 510 mg (1.9 mmol) of [1β,2α(Z),3β,4β]-7-[3-(hydroxymethyl)-7-oxabicyclo[2.2.1]hept-2-yl]-5-heptenoic acid, methyl ester (prepared as described in U.S. Pat. No. 4,143,054) in 10 ml of dry pyridine under argon at 0° C. was added a solution of 730 mg (3.8 mmol) of tosyl chloride in 10 ml of dry CH$_2$Cl$_2$. This mixture was allowed to warm to room temperature and stirred for 19 hours. The reaction mixture was poured into 70 ml of a mixture of ice and water and stirred for 40 minutes. The aqueous layer was extracted with ether (3×140 ml). The combined ether extracts were washed with 1N aqueous HCl solution (2×50 ml), saturated NaHCO$_3$ solution (2×50 ml) and brine (1×100 ml). The ether layer was dried (MgSO$_4$), filtered and concentrated in vacuo to give an oily product. This was chromatographed on 66 g of silica gel 60 using 1:1 hexane-ether as eluant to give 650 mg (81%) of desired title tosylate as an oil.

TLC: silica gel, hexane-ether 1:1, R$_f$=0.25, iodine.
Analysis: Calculated for C$_{22}$H$_{30}$O$_6$S: C, 62.53; H, 7.16; S, 7.59. Found: C, 62.12, H, 7.23; S, 7.41.

B.

[1β,2α(Z),3β,4β]-7-[3-[[(3-Phenyl-2-propenyl)thio]methyl]-7-oxabicyclo[2.2.1]hept-2-yl]-5-heptenoic acid, methyl ester Following the procedure of Example 1 except substituting the Part A tosylate for the Example 1B tosylate, the title compound is obtained.

EXAMPLE 6

[1β,2α(Z),3β(E),4β]-7-[3-[[(3-Phenyl-2-propenyl)thio]methyl]-7-oxabicyclo[2.2.1]hept-2-yl]-5-heptenoic acid Following the procedure of Example 2 except substituting the Example 5 methyl ester for the Example 1 methyl ester, the title compound is obtained.

EXAMPLE 7

[1S-[1α,2β(Z),3β(Z),4α]]-7-[3-[(3-Hexenylthio)methyl]-7-oxabicyclo[2.2.1]hept-2-yl]-5-heptenoic acid, methyl ester To a stirred solution of 91 mg (0.80 mmol) of potassium t-butoxide in 5 ml of dry THF under argon was added 426 mg (3.67 mmol) of cis-3-hexenyl mercaptan (prepared from cis-3-hexene-1-ol by the method of Volente; *Tetrahedron Letters*, 1981, 22, 3119). To this mixture was added a solution of 310 mg (0.73 mmol) of tosylate (prepared as described in Example 1, Part B) in 6 ml of dry THF. The reaction mixture was heated to reflux for 5 hours and 45 minutes. The cooled reaction mixture was diluted with 300 ml of ether and washed with 0.5N aqueous NaOH solution (2×70 ml), saturated NaHCO$_3$ solution (1×70 ml) and brine (1×100 ml). The ether solution was dried (MgSO$_4$), filtered and concentrated in vacuo to give an oily product. Purification was effected by flash chromatography on 30 g of silica gel 60 using hexane-ether (4:1) as eluant to give 240 mg of methyl ester as an oil (89%). TLC=silica gel, hexane-ether 1:1, R$_f$=0.64, iodine. [α]$_D$=−9.0 (c=2.47, CHCl$_3$).

EXAMPLE 8

[1S-[1α,2β(Z),3β(Z),4α]]-7-[3-[(3-Hexenylthio)methyl]-7-oxabicyclo[2.2.1]hept-2-yl]-5-heptenoic acid To a stirred solution of 240 mg (0.66 mmol) of Example 7 methyl ester in 3.0 ml of freshly distilled THF and 0.70 ml of H$_2$O under argon was added a small amount of hydroquinone (~5 mg) and 1.30 ml of 1N aqueous lithium hydroxide solution. This brown-colored mixture was purged with argon for 10 minutes and stirred at room temperature for 7 hours. The reaction mixture was acidified to pH 3 by the addition of 1N aqueous HCl solution and poured into 70 ml of saturated NaCl solution. The resulting solution was saturated with solid NaCl and extracted with EtOAc (5×70 ml). The combined EtOAc extracts were dried (MgSO$_4$), filtered and concentrated in vacuo to give title acid (120 mg, 52%). TLC=silica gel, 4% CH$_3$OH in CH$_2$Cl$_2$, R$_f$=0.41, iodine. [α]$_D$=−8.6° (c=1.82, CHCl$_3$).

Anal Calcd for C$_{20}$H$_{32}$O$_3$S: C, 68.14; H, 9.15; S, 9.10. Found: C, 67.74; H, 9.07; S, 8.79.

EXAMPLE 9

[1S-[1α,2β(Z),3β(E),4α]]-7-[3-[[(2-Methyl-2-hexenyl)-thio]methyl]-7-oxabicyclo[2.2.1]hept-2-yl]-5-heptenoic acid, methyl ester To a stirred solution of 70.4 mg (0.63 mmol) of potassium t-butoxide in 5 ml of dry THF under argon was added 230 mg (1.71 mmol) of E-2-methyl-2-hexenyl mercaptan (prepared from E-2-methyl-2-hexene-1-ol by the method of Volante; *Tetrahedron Letters,* 1981, 22, 3119). To this mixture was added a solution of 240 mg (0.57 mmol) of Example 1 Part B tosylate in 6 ml of dry THF. The reaction mixture was heated for 6 hours. The cooled reaction mixture was diluted with 50 ml of saturated $NaHCO_3$ solution and extracted with ether (3×70 ml). The combined ether extracts were washed with 0.5N aqueous NaOH solution (2×50 ml), $H_2O$ (1×50 ml) and brine (1×100 ml). The ether extracts were dried ($MgSO_4$), filtered and concentrated in vacuo to give 310 mg of an oily product. Purification was effected by flash chromatography on 28 g of silica gel 60 using hexane-ether (4:1) as eluant to give 140 mg (65%) of title methyl ester as an oil. TLC: silica gel, hexane-ether 2:1, $R_f$=0.60, iodine.

$[α]_D$= −11.7° (c=2.31, $CHCl_3$).

EXAMPLE 10

[1S-[1α,2β(Z),3β(E),4α]]-7-[3-[[(2-Methyl-2-hexenyl)-thio]methyl]-7-oxabicyclo[2.2.1]hept-2-yl]-5-heptenoic acid To a stirred solution of 120 mg (0.32 mmol) of Example 9 methyl ether in 16 ml of freshly distilled THF and 3 ml of $H_2O$ under argon was added a small amount of hydroquinone (∼5 mg) and 3.2 ml of 1N aqueous lithium hydroxide solution. This brown colored mixture was purged with argon vigorously for 20 minutes and stirred at room temperature for 7 hours. The reaction mixture was acidified to pH 3 by the addition of 1N aqueous HCl solution and poured into 50 ml of saturated NaCl solution. The resulting solution was saturated with solid NaCl and extracted with EtOAc (4×60 ml). The combined EtOAc extracts were dried ($MgSO_4$), filtered and concentrated in vacuo to give 150 mg of crude acid. Purification was effected by flash chromatography on 25 g of silica gel 60 using 2% $CH_3OH$ in $CH_2Cl_2$ as eluant to give title acid (110 mg, 95%). TLC: silica gel, 2% $CH_3OH/CH_2Cl_2$, $R_f$=0.20, iodine.

$[α]_D$= −11.6° (c=0.79, $CHCl_3$).

Anal Calcd for $C_{21}H_{34}O_3S$: C, 68.81; H, 9.35; S, 8.75. Found: C, 68.41; H, 9.33; S, 8.57.

EXAMPLE 11

[1S-[1α,2β(Z),3β(E),4α]]-7-[3-(2-Hexenylthio)methyl]-7-oxabicyclo[2.2.1]hept-2-yl]-5-heptenoic acid, methyl ester To a stirred solution of 88 mg (0.78 mmol) of potassium t-butoxide in 5 ml of dry THF under argon was added 247 mg (2.13 mmol) of trans-2-hexenyl mercaptan (prepared from trans-2 hexene-1-ol by the method of Volante; *Tetrahedron Letters,* 1981, 22, 3119). To this mixture was added a solution of 300 mg (0.71 mmol) of Example 1 Part B tosylate in 5 ml of dry THF. The reaction mixture was heated to reflux for 6 hours. The cooled reaction mixture was diluted with 350 ml of ether and washed with 75 ml of saturated $NaHCO_3$ solution. The ether solution was dried ($MgSO_4$), filtered and concentrated in vacuo. This was chromatographed on 30 g of silica gel 60 using hexane-ether (4:1) as eluant to give 182 mg of title methyl ester as an oil (73%). TLC=silica gel, hexane-ether 1:1, $R_f$=0.56, iodine. $[α]_D$= −11.5° (c=0.65, $CHCl_3$).

EXAMPLE 12

[1S-[1α,2β(Z),3β(E),4α]]-7-[3-(2-Hexenylthio)methyl]-7-oxabicyclo[2.2.1]hept-2-yl]-5-heptenoic acid To a stirred solution of 170 mg (0.48 mmol) of Example 11 methyl ester in 28 ml of freshly distilled THF and 4.7 ml of $H_2O$ under argon was added a small amount of hydroquinone (∼10 mg) and 5.0 ml of 1N aqueous lithium hydroxide solution. This brown-colored mixture was purged with argon vigorously for 10 minutes and stirred at room temperature for 7 hours and 30 minutes. The reaction mixture was acidified to pH 3 by the addition of 1N aqueous HCl solution and poured into 75 ml of saturated NaCl solution. The resulting solution was saturated with NaCl and extracted with EtOAc (4×80 ml). The combined EtOAc extracts were dried ($Na_2SO_4$), filtered and concentrated in vacuo. Purification was effected by flash chromatography on 25 g of silica gel 60 using 2% $CH_3OH$ in $CH_2Cl_2$ as eluant to give pure title acid (120 mg; 74%) as an oil. TLC=silica gel, 4% $CH_3OH/CH_2Cl_2$, $R_f$=0.24, iodine. $[α]_D$= −9.5° (c=0.84, $CHCl_3$).

Anal. Calcd for $C_{20}H_{32}O_3S$: C, 68.14; H, 9.15; S, 9.10. Found: C, 67.78; H, 8.80; S, 8.74.

EXAMPLE 13

[1S-[1β,2α(Z),3α,4β]]-7-[3-[(2-Propenylthio)methyl]-7-oxabicyclo[2.2.1]hept-2-yl]-5-heptenoic acid, methyl ester To a stirred solution of 88 mg (0.78 mmol) of potassium t-butoxide in 5 ml of dry THF under argon was added 158 mg (2.13 mmol) of allyl mercaptan. To this mixture was added a solution of 300 mg (0.71 mmol) of Example 1 Part B tosylate in 6 ml of dry THF. The reaction mixture was heated to reflux for 5 hours. The cooled reaction mixture was diluted with 200 ml of ether and poured into 100 ml of saturated $NaHCO_3$ solution. The aqueous layer was extracted with ether (2×120 ml). The combined ether extracts (440 ml) was washed with 0.5N aqueous sodium hydroxide solution (2×100 ml), $H_2O$ (1×100 ml) and brine (1×150 ml). The ether layer was dried over anhydrous $MgSO_4$, filtered and concentrated in vacuo to give an oily product. Purification was effected by chromatography on 28 g of silica gel 60 using hexane-ether 5:1 as eluant to give 200 mg (91%) of title methyl ester as an oil. TLC: silica gel, hexane-ether 2:1, $R_f$=0.60, iodine. $[α]_D$= −8.40° (c=1.27, $CHCl_3$).

EXAMPLE 14

[1S-[1β,2α(Z),3α,4β]]-7-[3-[(2-Propenylthio)methyl]-7-oxabicyclo[2.2.1]hept-2-yl]-5-heptenoic acid To a stirred solution of 190 mg (0.61 mmol) of Example 13 methyl ester in 31 ml of freshly distilled THF and 5.20 ml of water under argon was added a small amount of hydroquinone (∼5 mg) and 6.0 ml of 1N aqueous lithium hydroxide solution. This brown colored mixture was purged with argon for 10 minutes and stirred at room temperature for 6 hours. The reaction mixture was acidified to pH 3 by the addition of 1N aqueous HCl solution and poured into 50 ml of saturated NaCl solution. The resulting solution was saturated with solid NaCl and extracted with EtOAc (4×60 ml). The combined EtOAc extracts were dried (MgSO$_4$), filtered and concentrated in vacuo to give 280 mg of crude acid. Purification was effected by flash chromatography on 25 g of silica gel 60 using 4% CH$_3$OH/CH$_2$Cl$_2$ as eluant to give title product (150 mg, 75%).

TLC: Silica gel, 3% CH$_3$OH/CH$_2$Cl$_2$, R$_f$=0.25, iodine.

[α]$_D$= −8.52° (c=1.24, CHCl$_3$).

Anal Calcd for C$_{17}$H$_{26}$O$_3$S: C, 65.77; H, 8.44; S, 10.33. Found: C, 65.53; H, 8.60; S, 10.18.

EXAMPLE 15

[1S-[1α,2β(Z),3β,4α]]-7-[3-[(3-Hexynylthio)methyl]-7-oxabicyclo[2.2.1]hept-2-yl]-5-heptenoic acid, methyl ester To a stirred solution of 88 mg (0.78 mmol) of potassium t-butoxide in 5 ml of dry THF under argon was added 243 mg (2.13 mmol) of 3-hexynyl-1-mercaptan (prepared from 3-hexyn-1-ol by the method of Volante; *Tetrahedron Letters*, 1981, 22, 3119). To this mixture was added a solution of 300 mg (0.71 mmol) of Example 1 Part B tosylate in 5 ml of dry THF. The reaction mixture was heated to reflux for 5 hours. The cooled reaction mixture was diluted with 350 ml of ether and washed with 75 ml of saturated NaHCO$_3$ solution. The ether solution was dried (MgSO$_4$), filtered and concentrated in vacuo. This was chromatographed on 30 g of silica gel 60 using 4:1 hexane-ether as eluant to give 210 mg of title methyl ester as an oil (84%). TLC=silica gel, hexane-ether 1:1, R$_f$=0.55, iodine. [α]$_D$= −5.7° (c=0.97, CHCl$_3$).

EXAMPLE 16

[1S-[1α,2β(Z), 3β,4α]]-7-[3-[(3-Hexynylthio)methyl]-7-oxabicyclo[2.2.1]hept-2-yl]-5-heptenoic acid To a stirred solution of 210 mg (0.60 mmol) of Example 15 methyl ester in 34 ml of freshly distilled THF and 5.80 ml of H$_2$O under argon was added a small amount of hydroquinone (∼10 mg) and 6.10 ml of 1N aqueous lithium hydroxide solution. This brown-colored mixture was purged with argon vigorously for 10 minutes and stirred at room temperature for 7 hours and 35 minutes. The reaction mixture was acidified to pH 3 by the addition of 1N aqueous HCl solution and poured into 100 ml of saturated sodium chloride solution. The resulting solution was saturated with NaCl and extracted with EtOAc (4×125 ml). The combined EtOAc extracts were dried (MgSO$_4$), filtered and concentrated in vacuo. Purification was effected by flash chromatography on 26.2 g of silica gel 60 using 2% CH$_3$OH in CH$_2$Cl$_2$ as eluant to give title acid, (160 mg, 79%). TLC=silica gel, 4% CH$_3$OH/CH$_2$Cl$_2$, R$_f$=0.24, iodine. [α]$_D$= −5.2°, (c=0.82, CHCl$_3$).

Anal Calcd for C$_{20}$H$_{30}$O$_3$S: C, 68.53; H, 8.63; S, 9.15. Found: C, 68.37; H, 8.61; S, 8.91.

EXAMPLE 17

[1β,2α(Z), 3α(E),4β]-7-[3-[[(4-Phenyl-2-butenyl)thio]methyl]-7-oxabicyclo[2.2.1]hept-2-yl]-5-heptenoic acid Following the procedure of Examples 1 and 2 except substituting 4-phenyl-2-butenylthiol for (E)-3-phenyl-2-propenylthiol, the title compound is obtained.

EXAMPLE 18

[1β,2α(Z), 3α(E), 4β]-7-[3-[[(3-Cyclohexyl-2-propenyl)thio]methyl]-7-oxabicyclo[2.2.1]hept-2-yl]-5-heptenoic acid Following the procedure of Examples 1 and 2 except substituting (E)-3-cyclohexyl-2-propenylthiol for (E)-3-phenyl-2-propenylthiol, the title compound is obtained.

EXAMPLE 19

(1β,2α,3α,4β)-7-[3-[[(4-Cyclohexyl-2-butenyl)thio]methyl]-7-oxabicyclo[2.2.1]hept-2-yl]heptanoic acid Following the procedure of Examples 3 and 4 except substituting 4-cyclohexyl-2-butenylthiol for 3-phenyl-2-propenylthiol, the title compound is obtained.

EXAMPLE 20

[1β,2α(Z),3α,4β]-7-[3-[[(2,3-Dimethyl-2-heptenyl)thio]methyl]-7-oxabicyclo[2.2.1]hept-2-yl]-5-heptenoic acid Following the procedure of Examples 1 and 2 except substituting 2,3-dimethyl-2-heptenylthiol for 3-phenyl-2-propenylthiol, the title compound is obtained.

EXAMPLE 21

[1β,2α(Z),3α,4β]-7-[3-[[(3-Ethyl-3-octenyl)thio]methyl]-7-oxabicyclo[2.2.1]hept-2-yl]-5-heptenoic acid Following the procedure of Examples 1 and 2 except substituting 3-ethyl-3-octenylthiol for 3-phenyl-2-propenylthiol, the title compound is obtained.

EXAMPLE 22

(1β,2α,3α,4β)-7-[3-[(5-Phenyl-4-pentenyl)thio]methyl]-7-oxabicyclo[2.2.1]hept-2-yl]heptanoic acid Following the procedure of Examples 3 and 4 except substituting 5-phenyl-4-pentenylthiol for 3-phenyl-2-propenylthiol, the title compound is obtained.

EXAMPLE 23

[1β,2α(Z),3α,4β]-7-[3-[[(8-Phenyl-5-octynyl)thio]methyl]-7-oxabicyclo[2.2.1]hept-2-yl]-5-heptenoic acid Following the procedure of Examples 15 and 16 except substituting 8-phenyl-5-octynylthiol for 3-hexynylthiol, the title compound is obtained.

EXAMPLE 24

[1β,2α(Z),3β,4β]-7-[3-[[(4-Cyclopropyl-4-methyl-3-butenyl)thio]methyl]-7-oxabicyclo[2.2.1]-hept-2-yl]-5-heptenoic acid Following the procedure of Examples 5 and 6 except substituting 4-cyclopropyl-4-methyl-3-butenylthiol for 3-phenyl-2-propenylthiol, the title product is obtained.

EXAMPLE 25

[1β,2α(Z),3β,4β]-7-[3-[[(9-Cyclohexyl-3-nonynyl)thio]methyl]-7-oxabicyclo[2.2.1]hept-2-yl]-5-heptenoic acid Following the procedure of Examples 5, 6, 15 and 16 except substituting 9-cyclohexyl-3-nonynylthiol for 3-hexynyl mercaptan, the title compound is obtained.

EXAMPLE 26

(1β,2α,3α,4β)-7-[3-[[(6-Heptynyl)thio]methyl]-7-oxabicyclo[2.2.1]hept-2-yl]heptanoic acid Following the procedure of Examples 3, 4, 15 and 16 except substituting 6-heptynylthiol for 3-hexynyl mercaptan, the title compound is obtained.

EXAMPLE 27

[1β,2α(Z),3α,4β]-7-[3-[[(6-Cyclohexyl-2-ethyl-3-methyl-2-hexenyl)thio]methyl]-7-oxabicyclo[2.2.1]-hept-2-yl]-5-heptenoic acid Following the procedure of Examples 1 and 2 except substituting 6-cyclohexyl-2-ethyl-3-methyl-2-hexenyl-thiol for 3-phenyl-2-propenylthiol, the title product is obtained.

EXAMPLE 28

[1β,2α(Z),3β,4β]-7-[3-[[(5-Chloro-2-pentenyl)thio]-methyl]-7-oxabicyclo[2.2.1]hept-2-yl]-5-heptenoic acid Following the procedure of Examples 5 and 6 except substituting 5-chloro-2-pentenylthiol for 3-phenyl-2-propenylthiol, the title product is obtained.

EXAMPLE 29

(1β,2α,3α,4β)-7-[3-[[(6-Ethoxy-2-hexenyl)thio]-methyl]-7-oxabicyclo[2.2.1]hept-2-yl]heptanoic acid Following the procedure of Examples 3 and 4 except substituting 6-ethoxy-2-hexenylthiol for 3-phenyl-2-propenylthiol, the title product is obtained.

EXAMPLE 30

[1β,2α(Z),3α,4β]-7-[3-[[2-(3-Phenyl-2-propenyl)thio]ethyl]-7-oxabicyclo[2.2.1]hept-2-yl]-5-heptenoic acid

A.

[1β,2α(Z),3α,4β]-7-[3-(2-Oxo)ethyl-7-oxabicyclo[2.2.1-]hept-2-yl]-5-heptenoic acid, methyl ester Into a dry 100 ml round bottom 3-necked flask containing a stir bar was added dried 12.9 g (37.7 mmoles) methoxymethyltriphenylphosphonium chloride ((C6H5)3P+-CH2OCH3Cl-) and 235 ml distilled toluene (stored over molecular sieves). The resulting suspension was stirred in an ice-bath, under argon, until cold and then a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1β,2α(5Z),3α,4β]-7-[3-formyl-7-oxabicyclo[2.2.1]hept-2-yl]-5-heptenoic acid, methyl ester in 60 ml toluene was added by means of a dropping funnel over a 35 minute period with the ice-bath still in place. The reaction was then quenched by addition of 2.3 g (39 mmol) acetic acid in 5 ml ether. The reaction mixture immediately turned pale yellow and was immediately poured into 200 ml satured NH4Cl, and extracted with ether (4×200 ml). The combined ether phases were washed with NaCl, saturated solution, and dried (MgSO4) and concentrated to yield a yellow oil in a white crystalline solid (phosphine oxide). The white solid was triturated with EtOAc and the mother liquor was purified by chromatography on an LPS-1 silica column. The fractions obtained were (A) [1β,2α(Z)-,3α,4β]-7-[3-(2-oxo)ethyl-7-oxabicyclo[2.2.1]hept-2-yl]-5-heptenoic acid, methyl ester, (B) [1β,2α(Z),3α,4β]-7-[3-(2-methoxy)ethendiyl-7-oxabicyclo[2.2.1]hept-2-yl]-5-heptenoic acid, methyl ester, and (C) [1β,2α(Z)-,3α,4β]-7-[3-(2,2-dimethoxy)ethyl-7-oxabicyclo[2.2.1]-hept-2-yl]-5-heptenoic acid, methyl ester.

Compounds (B) and (C) are each treated with trifluoroacetic acid to convert each to compound (A).

B.

[1β,2α(Z),3α,4β]-7-[3-(2-Hydroxyethyl)-7-oxabicyclo[2.2.1]hept-2-yl]-5-heptenoic acid, methyl ester The aldehyde (1.4 g, 5 mmol) from part A in methanol (50 ml) is treated with NaBH4 (0.19 g, 5 mmol) in an argon atmosphere at 0° C. After stirring at 0° for 1 hour, the reaction is quenched by addition of 2N HCl (to pH 2). The methanol is removed in vacuo and the reaction mixture is taken up in ether. The ether solution is washed with saturated KHCO3, saturated NaCl and dried (MgSO4). The ether is evaporated to yield the title B compound.

C.

[1β,2α(Z),3α,4β]-7-[3-[[2-(3-Phenyl-2-propenyl)thio]ethyl]-7-oxabicyclo[2.2.1]hept-2-yl]-5-heptenoic acid Following the procedure of Examples 1 and 2 except substituting the above part B alcohol for the alcohol used in Example 1 Part B, the title compound is obtained.

EXAMPLE 31

[1β,2α(Z),3β,4β]-7-[3-[[2-(3-Phenyl-2-propenyl)thio]ethyl]-7-oxabicyclo[2.2.1]hept-2-yl]-5-heptenoic acid Following the procedure of Example 30 except substituting [1β,2α(Z),3β,4β]-7-[3-formyl-7-oxabicyclo[2.2.1]hept-2-yl]-5-heptenoic acid, methyl ester for [1β,2α(Z),3α,4β]-7-[3-formyl-7-oxabicyclo[2.2.1]hept-2-yl]-5-heptenoic acid, the title compound is obtained.

EXAMPLE 32

(1β,2α,3α,4β)-7-[3-[[2-(3-Phenyl-2-propenyl)thio]ethyl]-7-oxabicyclo[2.2.1]hept-2-yl]heptanoic acid Following the procedure of Example 30 except substituting (1β,2α,3α,4β)-7-[3-formyl-7-oxabicyclo[2.2.1]hept-2-yl]heptanoic acid, methyl ester for [1β,2α(5Z)-,3α,4β]-7-[3-formyl-7-oxabicyclo[2.2.1]hept-2-yl]-5-heptenoic acid, methyl ester, the title compound is obtained.

EXAMPLE 33

[1β,2α(Z),3α,4β]-7-[3-[[2-(6-Phenyl-3-hexynyl)-thio]ethyl]-7-oxabicyclo[2.2.1]hept-2-yl]-5-heptenoic acid Following the procedure of Examples 15, 16 and 30 except substituting 6-phenyl-3-hexynylthiol for 3-phenyl-2-propenylthiol, the title compound is obtained.

EXAMPLE 34

[1β,2α(Z),3β,4β]-7-[3-[[2-(5-Cyclopentyl-3-pentynyl)-thio]ethyl]-7-oxabicyclo[2.2.1]-hept-2-yl]-5-heptenoic acid Following the procedure of Example 15, 16 and 31 except substituting 5-cyclopentyl-3-pentynylthiol for 3-phenyl-2-propenylthiol, the title compound is obtained.

EXAMPLE 35

(1β,2α,3α,4β)-7-[3-[[2-(2-Ethyl-3-methyl-2-heptenyl)thio]ethyl]-7-oxabicyclo[2.2.1]-hept-2-yl]heptanoic acid Following the procedure of Example 32 except substituting 2-ethyl-3-methyl-2-heptenyl for 3-phenyl-2-propenylthiol, the title compound is obtained.

EXAMPLE 36

[1β,2α(Z),3α,4β]-7-[3-[[2-(3-Cycloheptyl-2-propenyl)thio]ethyl]-7-oxabicyclo[2.2.1]hept-2-yl]-5-heptenoic acid Following the procedure of Example 30 except substituting 3-cycloheptyl-2-propenylthiol for 3-phenyl-2-propenylthiol, the title compound is obtained.

EXAMPLE 37

[1β,2α(Z),3β,4β]-7-[3-[[2-(3-Hexenyl)thio]ethyl]-7-oxabicyclo[2.2.1]hept-2-yl]-5-heptenoic acid Following the procedure of Example 31 except substituting 3-hexenylthiol for 3-phenyl-2-propenylthiol, the title compound is obtained.

EXAMPLE 38

[1β,2α(Z),3α,4β]-7-[3-[[2-(4-Nonenyl)thio]ethyl]-7-oxabicyclo[2.2.1]hept-2-yl]-5-heptenoic acid Following the procedure of Example 30 except substituting 4-nonenylthiol for 3-phenyl-2-propenylthiol, the title compound is obtained.

EXAMPLE 39

[1β,2α(Z),3α,4β]-7-[3-[[2-(5-Phenyl-4-heptenyl)-thio]ethyl]-7-oxabicyclo[2.2.1]hept-2-yl]-5-heptenoic acid Following the procedure of Example 30 except substituting 5-phenyl-4-heptenylthiol for 3-phenyl-2-propenylthiol, the title compound is obtained.

EXAMPLE 40

[1β,2α(Z),3α,4β]-7-[3-[[2-(7-Octenyl)thio]ethyl]-7-oxabicyclo[2.2.1]hept-2-yl]-5-heptenoic acid Following the procedure of Example 30 except substituting 7-octenylthiol for 3-phenyl-2-propenylthiol, the title compound is obtained.

EXAMPLE 41

[1β,2α(Z),3β,4β]-7-[3-[[2-(4-Pentenyl)thio]ethyl]-7-oxabicyclo[2.2.1]hept-2-yl]-5-heptenoic acid Following the procedure of Example 31 except substituting 4-pentenylthiol for 3-phenyl-2-propenylthiol, the title compound is obtained.

EXAMPLE 42

[1β,2α(Z),3α,4β]-7-[3-[[2-(4-Cyclopentyl-3-butenyl)thio]ethyl]-7-oxabicyclo[2.2.1]hept-2-yl]-5-heptenoic acid Following the procedure of Example 30 except substituting 4-cyclopentyl-3-butenylthiol for 3-phenyl-2-propenylthiol, the title compound is obtained.

EXAMPLE 43

[1β,2α(Z),3α,4β]-7-[3-[[2-(8-Phenyl-4-octenyl)thio]ethyl]-7-oxabicyclo[2.2.1]hept-2-yl]-5-heptenoic acid Following the procedure of Example 30 except substituting 8-phenyl-4-octenylthiol for 3-phenyl-2-propenylthiol, the title compound is obtained.

EXAMPLE 44

[1β,2α(Z),3α,4β]-7-[3-[[4-(3-Phenyl-2-propenyl)thio]butyl]-7-oxabicyclo[2.2.1]hept-2-yl]-5-heptenoic acid

A.

[1β,2α(Z),3α,4β]-7-[3-(3-Oxo)propyl-7-oxabicyclo[2.2.1]hept-2-yl]-5-heptenoic acid, methyl ester Following the procedure of Example 30 Part A except substituting [1β,2α(Z),3α,4β]-7-[3-(2-oxo)-ethyl-7-oxabicyclo[2.2.1]hept-2-yl]-5-heptenoic acid, methyl ester for [1β,2α(Z),3α,4β]-7-[3-formyl-7-oxabicyclo[2.2.1]hept-2-yl]-5-heptenoic acid, methyl ester, the title A compound is obtained.

B.

[1β,2α(Z),3α,4β]-7-[3-(4-Oxo)butyl-7-oxabicyclo[2.2.1]hept-2-yl]-5-heptenoic acid, methyl ester Following the procedure of Example 30 Part A except substituting the aldehyde from Part A above for [1β,2α(Z),3α,4β]-7-[3-formyl-7-oxabicyclo[2.2.1]hept-2-yl]-5-heptenoic acid, methyl ester, the title B compound is obtained.

C.

[1β,2α(Z),3α,4β]-7-[3-(4-Hydroxybutyl)-7-oxabicyclo[2.2.1]hept-2-yl]-5-heptenoic acid, methyl ester Following the procedure of Example 30 Part B except substituting the title B aldehyde for [1β,2α(Z),3α,4β]-7-[3-(2-oxo)ethyl]-7-oxabicyclo[2.2.1]hept-2-yl]-5-heptenoic acid, methyl ester, the title C alcohol is obtained.

D. [1β,2α(Z),3α,4β]-7-[3-[[4-(3-Phenyl-2-propenyl)thio]butyl]-7-oxabicyclo[2.2.1]hept-2-yl]-5-heptenoic acid Following the procedure of Examples 1 and 2 except substituting the above Part C alcohol for the alcohol used in Example 1, the title compound is obtained.

EXAMPLE 45

[1β,2α(Z),3α,4β]-7-[3-[[4-(6-Phenyl-3-hexynyl)thio]butyl]-7-oxabicyclo[2.2.1]hept-2-yl]-5-heptenoic acid Following the procedure of Examples 15, 16 and 44 except substituting 6-phenyl-3-hexynylthiol for 3-phenyl-2-propenylthiol, the title compound is obtained.

EXAMPLE 46

[1β,2α(Z),3α,4β]-7-[3-[[4-(7-Phenyl-3-heptenyl)thio]butyl]-7-oxabicyclo[2.2.1]hept-2-yl]-5-heptenoic acid Following the procedure of Example 44 except substituting 7-phenyl-3-heptenylthiol for 3-phenyl-2-propenylthiol, the title compound is obtained.

EXAMPLE 47

(1β,2α,3α,4β)-7-[3-[[4-(6-Hexenyl)thio]butyl]-7-oxabicyclo[2.2.1]hept-2-yl]heptanoic acid Following the procedure of Examples 3, 4 and 44 except substituting 6-hexenylthiol for 3-phenyl-2-propenylthiol, the title compound is obtained.

EXAMPLE 48

[1β,2α(Z),3α,4β]-7-[3-[[4-(7-Heptynyl)thio]butyl]-7-oxabicyclo[2.2.1]hept-2-yl]-5-heptenoic acid Following the procedure of Examples 15, 16 and 44 except substituting 7-heptynylthiol for 3-phenyl-2-propenylthiol, the title compound is obtained.

EXAMPLE 49

[1β,2α(Z),3α,4β]-7-[3-[[4-(5-Phenyl-3-pentynyl)thio]butyl]-7-oxabicyclo[2.2.1]hept-2-yl]-5-heptenoic acid Following the procedure of Examples 15, 16 and 44 except substituting 5-phenyl-3-pentynylthiol for 3-phenyl-2-propenylthiol, the title compound is obtained.

EXAMPLE 50

[1β,2α(Z),3α,4β]-7-[3-[[4-(5-Cyclohexyl-2-pentenyl)thio]butyl]-7-oxabicyclo[2.2.1]hept-2-yl]-5-heptenoic acid Following the procedure of Example 44 except substituting 5-cyclohexyl-2-pentenylthiol for 3-phenyl-2-propenylthiol, the title compound is obtained.

EXAMPLES 51, 52 AND 53

[1β,2α(Z),3α,4β]-7-[3-[[(3-Phenyl-2-propenyl)sulfinyl]methyl]-7-oxabicyclo[2.2.1]hept-2-yl]-5-heptenoic acid, methyl ester (fast moving isomer)

[1β,2α(Z),3α,4β]-7-[3-[[(3-Phenyl-2-propenyl)sulfinyl]methyl]-7-oxabicyclo[2.2.1]hept-2-yl]-5-heptenoic acid, methyl ester (slow moving isomer)

and

[1β,2α(Z),3α,4β]-7-[3-[[(3-Phenyl-2-propenyl)sulfonyl]methyl]-7-oxabicyclo[2.2.1]hept-2-yl]-5-heptenoic acid, methyl ester To a solution of 691 mg (1.72 mmol) of [1β,2α(Z),3α,4β]-7-[3-(3-phenyl-2-propenyl)methyl]-7-oxabicyclo[2.2.1]hept-2-yl]-5-heptenoic acid, methyl ester (prepared as described in Example 1) in 6.78 ml of methanol at 0° C. is added dropwise over 4 minutes 8.37 ml of 0.5M aqueous sodium periodate solution. Tetrahydrofuran (2 ml) is then added and the resulting reaction mixture is stirred at room temperature for 15 hours. A white precipitate is removed by filtration and washed with ether (3×50 ml). The filtrate is washed with 60 ml of saturated aqueous NaHCO3 solution and dried over anhydrous magnesium sulfate. Concentration in vacuo affords an oily crude product. This is chromatographed on 54 g of silica gel 60 using 0.5–1.0% CH3OH in CH2Cl2 as eluent. This gives FMI (fast moving isomer) sulfoxide (Example 51), SMI (slow moving isomer) sulfoxide (Example 52) and sulfone (Example 53).

EXAMPLE 54

[1β,2α(Z),3α,4β]-7-[3-[[(3-Phenyl-2-propenyl)sulfonyl]methyl]-7-oxabicyclo[2.2.1]hept-2-yl]-5-heptenoic acid To a stirred solution of 165 mg (0.41 mmol) of [1β,2α(Z),3α,4β]-7-[3-[[(3-phenyl-2-propenyl)sulfonyl]methyl]-7-oxabicyclo[2.2.1]hept-2-yl]-5-heptenoic acid, methyl ester (Example 53) in 20.3 ml of THF and 3.09 ml of H2O under argon is added 3.90 ml of 1N aqueous lithium hydroxide solution. This mixture is purged with argon vigorously for 10 minutes and stirred at room temperature for 6 hours. The reaction mixture is acidified to pH 4 by addition of 1N aqueous HCl solution and poured into 30 ml of saturated NaCl solution. The resulting solution is saturated with solid NaCl and extracted with EtOAc (4×50 ml). The combined EtOAc extracts are dried (MgSO4), filtered and concentrated in vacuo to give the crude acid. Purification is effected by flash chromatography on 20 g of silica gel 60 using 3% CH3OH in CH2Cl2 as eluant. This affords the title acid.

EXAMPLE 55

[1β,2α(Z),3α,4β]-7-[3-[[(3-Phenyl-2-propenyl)sulfinyl]methyl]-7-oxabicyclo[2.2.1]hept-2-yl]-5-heptenoic acid (fast moving isomer)

To a stirred solution of 212 mg (0.55 mmol) of [1β,2α(Z),3α,4β]-7-[3-[[(3-phenyl-2-propenyl)sulfinyl]methyl]-7-oxabicyclo[2.2.1]hept-2-yl]-5-heptenoic acid, methyl ester (faster moving isomer) prepared in Example 51 in 27.0 ml of THF and 4.11 ml of H2O under argon is added 5.19 ml of 1N aqueous lithium hydroxide solution. This mixture is purged with argon vigorously for 10 minutes and stirred at room temperature for 6 hours. The reaction mixture is acidified to pH 4 by addition of 1N aqueous HCl solution and poured into 50 ml of saturated NaCl solution. The resulting solution is saturated with solid NaCl and extracted with EtOAc (4×100 ml). The combined EtOAc extracts are dried (MgSO4), filtered and concentrated in vacuo to give the crude acid. Purification is effected by flash chromatography on 20.2 g of silica gel 60 using 3% CH3OH in CH2Cl2 as eluant to give the title acid.

EXAMPLE 56

[1β,2α(Z),3α,4β]-7-[3-[[(4-Cyclohexyl-2-butenyl)sulfinyl]methyl]-7-oxabicyclo[2.2.1]hept-2-yl]-5-heptenoic acid Following the procedure of Examples 1, 51 and 55 except substituting 4-cyclohexyl-2-butenylthiol for 3-phenyl-2-propenylthiol, the title compound is obtained.

EXAMPLE 57

[1β,2α(Z),3α,4β]-7-[3-[[(6-Hexenyl)sulfinyl]methyl]-7-oxabicyclo[2.2.1]hept-2-yl]-5-heptenoic acid Following the procedure of Examples 1, 51 and 55 except substituting 6-hexenylthiol for 3-phenyl-2-propenylthiol, the title compound is obtained.

EXAMPLE 58

[1β,2α(Z),3β,4β]-7-[3-[[(6-Phenyl-3-hexynyl)sulfinyl]methyl]-7-oxabicyclo[2.2.1]hept-2-yl]-5-heptenoic acid Following the procedure of Examples 15, 16, 5, 51 and 55 except substituting 6-phenyl-3-hexynylthiol for 3-phenyl-2-propenylthiol, the title compound is obtained.

EXAMPLE 59

[1β,2α(Z),3β,4β]-7-[3-[[(4-Ethyloxy-2butenyl)sulfinyl]methyl]-7-oxabicyclo[2.2.1]hept-2-yl]-5-heptenoic acid Following the procedure of Examples 5, 51 and 55 except substituting 4-ethyloxy-2-butenylthiol for 3-phenyl-2-propenylthiol, the title compound is obtained.

EXAMPLE 60

[1β,2α(Z),3β,4β]-7-[3-[[(8-Octenyl)sulfonyl]methyl]-7-oxabicyclo[2.2.1]hept-2-yl]-5-heptenoic acid Following the procedure of Examples 5, 51 and 54 except substituting 8-octenylthiol for 3-phenyl-2-propenylthiol, the title compound is obtained.

EXAMPLE 61

[1β,2α(Z),3α,4β]-7-[3-[[(5-Cyclohexyl-2-methyl-2-pentenyl)sulfonyl]methyl]-7-oxabicyclo[2.2.1]hept-2-yl]-5-heptenoic acid Following the procedure of Examples 1, 51 and 54 except substituting 5-cyclohexyl-2-methyl-2-pentenylthiol for 3-phenyl-2-propenylthiol, the title compound is obtained.

EXAMPLE 62

[1β,2α(Z),3α,4β]-7-[3-[[(4-Hexenyl)sulfonyl]methyl]-7-oxabicyclo[2.2.1]hept-2-yl]-5-heptenoic acid Following the procedure of Examples 1, 51 and 54 except substituting 4-hexenylthiol for 3-phenyl-2-propenylthiol, the title compound is obtained.

EXAMPLE 63

[1β,2α(Z),3α,4β]-7-[3-[[(3-Heptynyl)sulfonyl]methyl]-7-oxabicyclo[2.2.1]hept-2-yl]-5-heptenoic acid Following the procedure of Examples 1, 51 and 54 except substituting 3-heptynylthiol for 3-phenyl-2-propenylthiol, the title compound is obtained.

EXAMPLES 64 AND 65

[1β,2α(6Z),3α,4β]-7-[3-[[(3-Phenyl-2-propenyl)thio]methyl]-7-oxabicyclo[2.2.1]hept-2-yl]-6-heptenoic acid
and
[1β,2β(6Z),3α,4β]-7-[3-[[(3-Phenyl-2-propenyl)thio]methyl]-7-oxabicyclo[2.2.1]hept-2-yl]-6-heptenoic acid

A.
[1β,2α(6Z),3α,4β]-7-[3-(Hydroxymethyl)-7-oxabicyclo[2.2.1]hept-2-yl]heptenoic acid, methyl ester
and

B.
[1β,2β(6Z),3α,4β]-7-[3-(Hydroxymethyl)-7-oxabicyclo[2.2.1]hept-2-yl]heptenoic acid, methyl ester A slurry of carboxypentyl triphenylphosphonium bromide in THF is cooled in an ice bath and treated dropwise with 1.4M KOt-amylate in toluene. After completion of this addition, the reaction mixture is allowed to warm to room temperature and is stirred for 6 hours. To this stirred solution is then added a solution of hemiacetal B (reaction sequence D) (prepared as described in Example 3 of U.S. Pat. No. 4,143,054) in THF dropwise over 30 minutes. The reaction mixture is then stirred overnight (15 hours). The mixture is cooled in an ice bath and quenched with HOAc. The solvent is removed in vacuo and the resulting residue is dissolved in saturated NaCl solution. This is extracted with chloroform. The chloroform layers are then extracted with saturated NaHCO₃ solution. The aqueous extracts are acidified to pH ~3.5 by addition of aqueous HCl solution, and then are extracted with several portions of chloroform. The combined chloroform extracts are concentrated in vacuo to afford the crude product. The crude acid is esterified with excess ethereal diazomethane at 0° C. and then is purified by chromatography on silica gel to afford the title esters.

C.
[1β,2α(6Z),3α,4β]-7-[3-[[3-Phenyl-2-propenyl)thio]methyl]-7-oxabicyclo[2.2.1]hept-2-yl]-6-heptenoic acid Following the procedure of Example 1 except substituting the title A and B methyl esters (prepared by reacting the acids with diazomethane) for the Example 1 part A ester, the title compound is obtained.

EXAMPLE 67

[1β,2α(5Z),3α,4β]-8-[3-[[(3-Phenyl-2-propenyl)thio]methyl]-7-oxabicyclo[2.2.1]hept-2-yl]-5-octenoic acid

A.
(1β,2α,3α,4β)-3-[3-(Hydroxymethyl)-7-oxabicyclo[2.2.1]hept-2-yl]propionaldehyde A slurry of methoxymethyltriphenylphosphonium chloride (1.09 kg, 3.18 mol) in Burdick and Jackson sieve-dried tetrahydrofuran (3 liters) was chilled to 0° C. and treated dropwise with 1.4M potassium t-amylate in toluene (1910 ml, 2.67 mol) over 20 minutes. The resultant dark red solution was stirred at 0° C. for 1 hour. The mixture was then treated slowly over 5 minutes with solid hemiacetal (B in reaction sequence D) prepared as described in Example 3 of U.S. Pat. No. 4,143,054 (200 g, 1.28 mol). The temperature gradually rose to 23° C. The mixture was stirred vigorously at room temperature for 90 minutes. The reaction mixture was then chilled to 0° C. and treated slowly with acetaldehyde (124 ml, 2.2 mol) over 10 minutes. The mixture was diluted with water (2500 ml) and treated with 10% hydrochloric acid to pH 7. The mixture was then extracted with ether (7×2 liters). The combined ether extracts were dried over magnesium sulfate, filtered, and the filtrates concentrated in vacuo. The resultant mixture was treated with isopropyl ether (4 liters) and stirred overnight. The mixture was chilled to −10° C. for 90 minutes then filtered. The solids were washed thoroughly with isopropyl ether. The filtrate was concentrated in vacuo to an oily residue (460 g). This oily residue was treated with water (4000 ml) and stirred vigorously for 2 hours. The aqueous layer was decanted and the oily residue treated two additional times with water (2×1 liter). After the third wash, the residue solidified and was filtered. The combined aqueous triturates were concentrated in vacuo to 3.5 liters. The cloudy mixture was filtered through a bed of Celite. The filtrate was concentrated again to a volume of 2.3 liters. The cloudy solution was chilled in an ice bath and treated slowly with concentrated hydrochloric acid (683 ml). The mixture was then stirred at room temperature for 3 hours. After this time the solution was neutralized by the slow addition of solid sodium bicarbonate (720 g). The mixture was filtered through a bed of Celite then extracted with hexane (4×2 liters) then ethyl acetate (10×2 liters). The combined ethyl acetate extracts were dried over MgSO₄ and concentrated in vacuo. The solid residue was triturated with hexane (1 liter), filtered, and dried in vacuo to yield 220 g (100%) of desired compound (hemiacetal C in reaction sequence F), m.p. 104°–105° C., [α]$_D$ = +27° c=1 MeOH.

TLC: Silica gel; EtOAc; R$_f$=0.3; Ce(SO₄)₂.

The above Wittig procedure was repeated on the hemiacetal C used in place of hemiacetal B to form the title aldehyde.

B.
[1β,2α(Z),3α,4β]-8-[3-(Hydroxymethyl)-7-oxabicyclo[2.2.1]hept-2-yl]-5-octenoic acid, methyl ester Following the procedure of Example 1 Part A except substituting the above title A aldehyde for the Example 1 Part A(b) compound, the title compound is obtained.

C.
[1β,2α(Z),3α,4β]-8-[3-[[(3-Phenyl-2-propenyl)thio]methyl]-7-oxabicyclo[2.2.1]hept-2-yl]-5-octenoic acid Following the procedure of Example 1 except substituting the title B ester for the Example 1 Part A acid in the form of its methyl ester (prepared by reacting the acid with diazomethane), the title compound is obtained.

EXAMPLES 68 AND 69

[1β,2α(2E),3α,4β]-7-[3-[[(3-Phenyl-2-propenyl)thio]methyl]-7-oxabicyclo[2.2.1]hept-2-yl]heptenoic acid and

[1β,2α(2Z),3α,4β]-7-[3-[[(3-Phenyl-2-propenyl)thio]methyl]-7-oxabicyclo[2.2.1]hept-2-yl]heptenoic acid

A.
[1β,2α,3α,4β]-5-[3-(Hydroxymethyl)-7-oxabicyclo[2.2.1]hept-2-yl]pentanal

Following the procedure of Example 67 Part A, except substituting (1β,2α,3α,4β)-3-[3-(hydroxymethyl)-7-oxabicyclo[2.2.1]hept-2-yl]propionaldehyde for the hemiacetal B (see reaction sequence D or F), (1β,2α,3α,4β)-4-[3-(hydroxymethyl)-7-oxabicyclo[2.2.1]hept-2-yl]butanal is obtained. Then by repeating the procedure of Example 67 Part A on (1β,2α,3α,4β)-4-[3-(hydroxymethyl)-7-oxabicyclo[2.2.1]hept-2-yl]butanal, the title A aldehyde is produced.

B.
[1β,2α(2E),3α,4β]-7-[3-(Hydroxymethyl)-7-oxabicyclo[2.2.1]hept-2-yl]heptenoic acid, methyl ester and

C.
[1β,2α(2Z),3α,4β]-7-[3-(Hydroxymethyl)-7-oxabicyclo[2.2.1]hept-2-yl]heptenoic acid, methyl ester To a stirred solution of the title A aldehyde in MeOH is added carbomethoxymethylene triphenylphosphorane. The resulting solution is stirred under argon at room temperature for 24 hours. The solvent is then removed in vacuo and the resultant viscous oil is triturated with ether. The precipitated triphenylphosphine oxide is removed by filtration and the filtrate is concentrated in vacuo to afford a mixture of the (E) and (Z) esters. Purification is affected by chromatography to afford the pure title esters.

D.
[1β,2α(2E),3α,4β]-7-[3-[[(3-Phenyl-2-propenyl)thio]methyl]-7-oxabicyclo[2.2.1]hept-2-yl]heptenoic acid and

E.
[1β,2α(2Z),3α,4β]-7-[3-[[(3-Phenyl-2-propenyl)thio]methyl]-7-oxabicyclo[2.2.1]hept-2-yl]heptenoic acid Following the procedure of Example 1 except substituting the title B and C esters for the Example 1 Part A acid in the form of its methyl ester (prepared by reacting the acid with diazomethane), the title compounds are obtained.

EXAMPLES 70 TO 84

Following the procedures outlined in the specification and described in the above working Examples, the following compounds may be prepared.

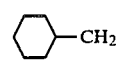

| Ex. No. | p | A | m | n | n' | q | X | t | R¹ |
|---|---|---|---|---|---|---|---|---|---|
| 70. | 2 | (CH₂)₂ | 0 | 1 | 2 | 1 | CH=CH | 0 | 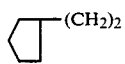 |
| 71. | 3 | (CH₂)₂ | 2 | 2 | 2 | 2 | C≡C | 1 | 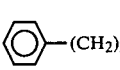 |
| 72. | 4 | CH=CH | 4 | 3 | 2 | 3 | CH=CH | 2 | 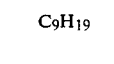 |
| 73. | 2 | (CH₂)₂ | 6 | 4 | 1 | 4 | C=CH<br>\|<br>CH₃ | 3 | C₉H₁₉ |
| 74. | 3 | CH=CH | 8 | 4 | 1 | 1 | C≡C | 4 | C₇H₁₅ |
| 75. | 4 | (CH₂)₂ | 0 | 3 | 2 | 2 | C≡C | 5 | C₂H₅ |
| 76. | 1 | (CH₂)₂ | 1 | 2 | 2 | 3 | CH=CH | 0 | CH₃ |
| 77. | 0 | CH=CH | 3 | 1 | 0 | 4 | CH=CH | 1 | 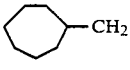 |

-continued

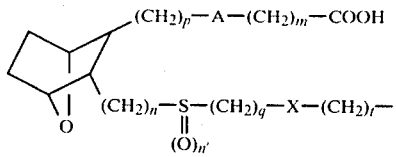

| Ex. No. | p | A | m | n | n' | q | X | t | R¹ |
|---|---|---|---|---|---|---|---|---|---|
| 78. | 2 | (CH₂)₂ | 5 | 1 | 0 | 3 | CH=CH | 2 | 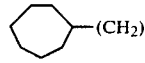—(CH₂)₂ |
| 79. | 0 | (CH₂)₂ | 7 | 2 | 2 | 2 | C≡C | 3 | C₆H₅ |
| 80. | 3 | (CH₂)₂ | 0 | 3 | 2 | 1 | C≡C | 4 |  |
| 81. | 4 | CH=CH | 0 | 4 | 1 | 2 | CH=CH | 5 |  |
| 82. | 0 | CH=CH | 2 | 3 | 2 | 4 | CH₃  CH₃<br> \|    \|<br>C=C | 4 | —(CH₂)₂ |
| 83. | 2 | (CH₂)₂ | 3 | 2 | 2 | 3 | C≡C | 2 | 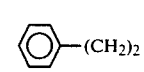 |
| 84. | 4 | (CH₂)₂ | 4 | 1 | 2 | 2 | C≡C | 0 | CH₃ |

What is claimed is:

1. A compound having the structural formula

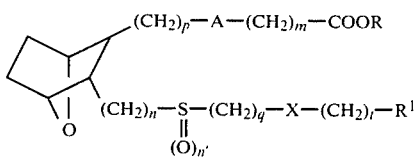

and including all stereoisomers thereof, wherein p is 0 to 4; A is CH=CH, (CH₂)₂, or a single bond; m is 0 to 8; R is H, lower alkyl, alkali metal or tris(hydroxymethyl)aminomethane; n is 1 to 4; n' is 0, 1 or 2; q is 1 to 12; X is

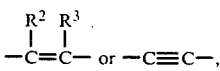

wherein R² and R³ may be the same or different and are H or lower alkyl; t is 0 to 5; and R¹ is H, lower alkyl, aryl, aralkyl, cycloalkyl or cycloalkylalkyl, wherein the term lower alkyl or alkyl by itself or as part of another group contains 1 to 12 carbons and is unsubstituted or substituted with halo, trifluoromethyl, alkoxy, haloaryl, cycloalkyl or alkylcycloalkyl;

the term aryl by itself or as part of another group contains 6 to 10 carbons and is unsubstituted or substituted with lower alkyl, halogen or lower alkoxy;

the term cycloalkyl by itself or as part of another group contains 3 to 12 carbons and is unsubstituted or substituted with 1 or 2 halogens, 1 or 2 lower alkyl groups and/or 1 or 2 lower alkoxy groups; and (CH₂)ₚ, (CH₂)ₘ, (CH₂)ₙ, (CH₂)_q and (CH₂)_t can contain one or more lower alkyl substituents.

2. The compound as defined in claim 1 wherein A is —CH=CH—.

3. The compound as defined in claim 1 wherein R is H.

4. The compound as defined in claim 1 wherein n' is 0.

5. The compound as defined in claim 1 wherein A is —CH=CH—, p is 1, m is 2 to 4, n is 1 or 2, n' is 0, q is 1 or 2; t is 0, 1 or 2, X is

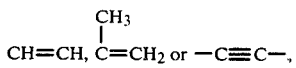

R is H or lower alkyl and R¹ is alkyl, H, aryl or aralkyl.

6. The compound as defined in claim 1 wherein p is 1, A is —CH=CH—, m is 3, n is 1, n' is 0, q is 2, X is CH=CH, C=CH₂ or —C≡C—,
          |
          CH₃

R is H, CH₃ or C₂H₅, and R¹ is lower alkyl or C₆H₅.

7. The compound as defined in claim 1 having the name [1β,2α(Z),3α(E),4β]-7-[3-[[(3-phenyl-2-propenyl)thio]methyl]-7-oxabicyclo[2.2.1]hept-2-yl]-5-heptenoic acid or the methyl or ethyl ester thereof including all stereoisomers thereof.

8. The compound as defined in claim 1 having the name [1S-[1α,2β(Z),3β(Z),4α]]-7-[3-[(3-hexenylthio)methyl]-7-oxabicyclo[2.2.1]hept-2-yl]-5-heptenoic acid or the methyl or ethyl ester thereof including all stereoisomers thereof.

9. The compound as defined in claim 1 having the name [1S-[1α,2β(Z),3β(E),4α]]-7-[3-[[(2-methyl-2-hexenyl)thio]methyl]-7-oxabicyclo[2.2.1]hept-2-yl]-5-heptenoic acid or the methyl or ethyl ester thereof including all stereoisomers thereof.

10. The compound as defined in claim 1 having the name [1S-[1α,2β(Z),3β(E),4α]]-7-[3-(2-hexenylthio)methyl]-7-oxabicyclo[2.2.1]hept-2-yl]-5-heptenoic acid or the methyl or ethyl ester thereof including all stereoisomers thereof.

11. The compound as defined in claim 1 having the name [1S-[1β,2α(Z),3α,4β]]-7-[3-[(2-propenylthio)methyl]-7-oxabicyclo[2.2.1]hept-2-yl]-5-heptenoic acid or the methyl or ethyl ester thereof including all stereoisomers thereof.

12. The compound as defined in claim 1 having the name [1S-[1α,2β(Z),3β,4α]]-7-[3-[(3-hexynylthio)methyl]-7-oxabicyclo[2.2.1]hept-2-yl]-5-heptenoic acid or the methyl or ethyl ester thereof including all stereoisomers thereof.

13. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

14. The method as defined in claim 13 wherein said compound is administered in an amount within the range of from about 1 to about 100 mg/kg.

15. A composition for inhibiting arachidonic acid-induced platelet aggregation and bronchoconstriction comprising an effective amount of a compound as defined in claim 1 or a pharmaceutically acceptable salt thereof, and a pharmaceutically acceptable carrier therefor.

16. A method of inhibiting platelet aggregation and bronchoconstriction or treating inflammation or relieving pain which comprises administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,560,698

DATED : December 24, 1985

INVENTOR(S) : Steven E. Hall et al.

It is certified that error appears in the above-identified patent and that said Letters Patent is hereby corrected as shown below:

Column 3, structure II should read

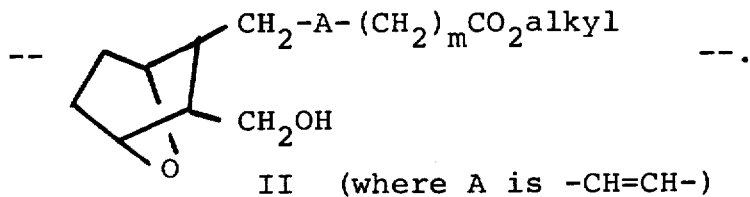

Column 4, structure VA should read

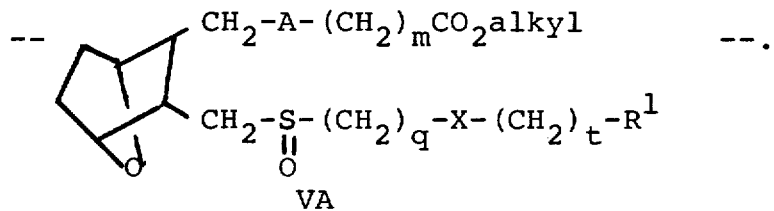

Column 7, structure VII should read

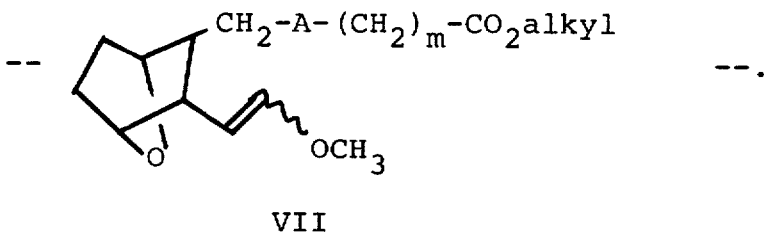

UNITED STATES PATENT AND TRADEMARK OFFICE
CERTIFICATE OF CORRECTION

PATENT NO. : 4,560,698
DATED : December 24, 1985
INVENTOR(S) : Steven E. Hall et al.

It is certified that error appears in the above—identified patent and that said Letters Patent is hereby corrected as shown below:

Column 9, structure C should read

-- 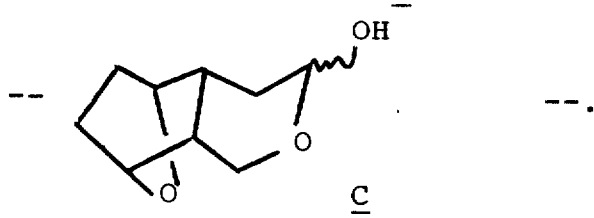 --.

C

Column 11, structure XVIA should read

-- 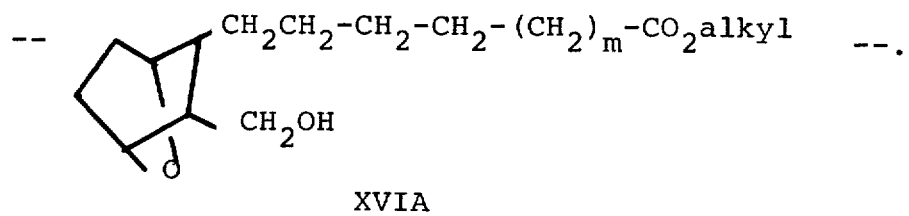 --.

XVIA

Columns 17 and 18, structures Ic, Id, Ie and If should read

-- Ic 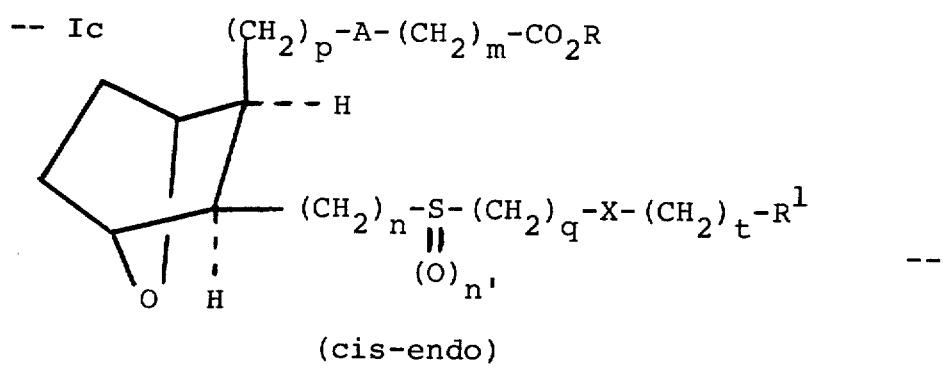 --

(cis-endo)

UNITED STATES PATENT AND TRADEMARK OFFICE
CERTIFICATE OF CORRECTION

PATENT NO. : 4,560,698
DATED : December 24, 1985
INVENTOR(S) : Steven E. Hall et al.

It is certified that error appears in the above—identified patent and that said Letters Patent is hereby corrected as shown below:

--

Id 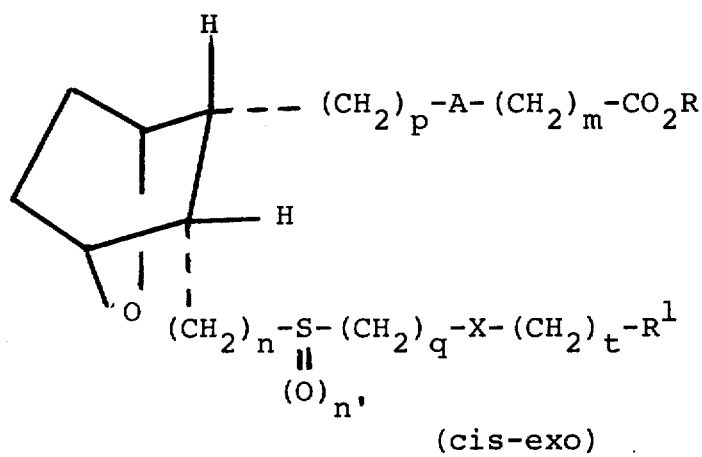

(cis-exo)

--

Ie 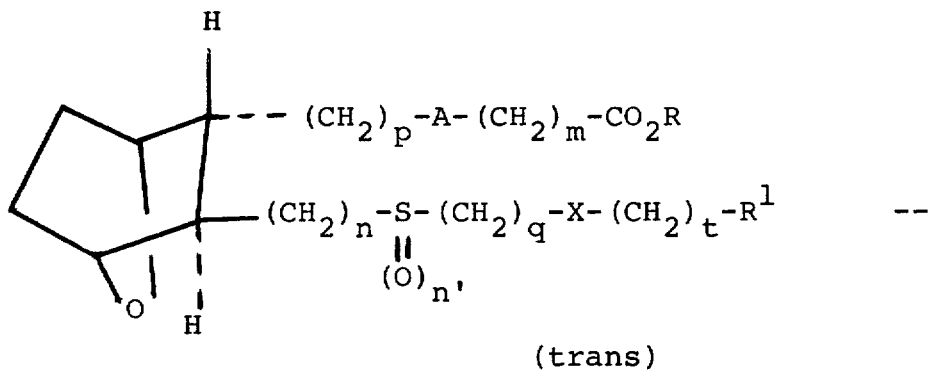

(trans)

UNITED STATES PATENT AND TRADEMARK OFFICE
CERTIFICATE OF CORRECTION

PATENT NO. : 4,560,698

DATED : December 24, 1985

INVENTOR(S) : Steven E. Hall et al.

It is certified that error appears in the above—identified patent and that said Letters Patent is hereby corrected as shown below:

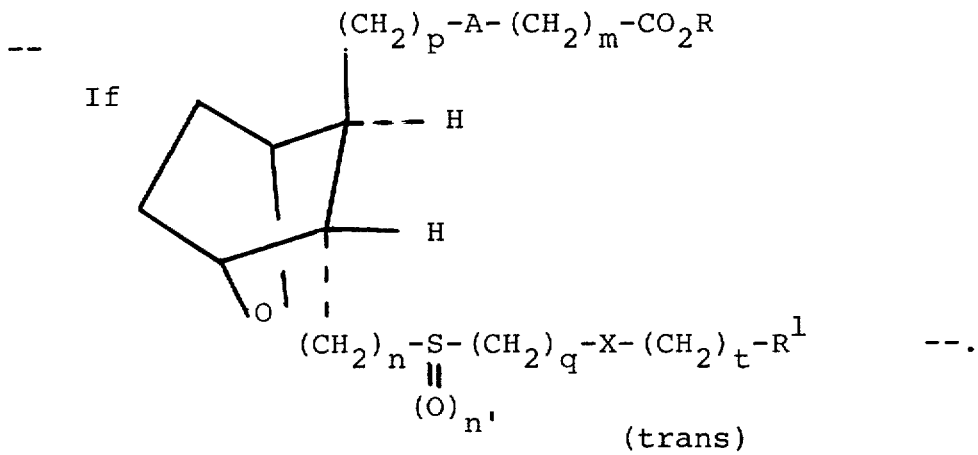

Signed and Sealed this

Eighteenth Day of November, 1986

*Attest:*

DONALD J. QUIGG

*Attesting Officer*  *Commissioner of Patents and Trademarks*